(12) United States Patent
Girardet et al.

(10) Patent No.: US 8,324,223 B2
(45) Date of Patent: Dec. 4, 2012

(54) SUBSTITUTED THIENO [2,3-D] PYRIMIDINES AS HIV INHIBITORS

(75) Inventors: Jean-Luc Girardet, San Diego, CA (US); Zhi Hong, Chapel Hill, NC (US); Stephanie Shaw, Rowland Heights, CA (US); Yung-hyo Koh, Irvine, CA (US)

(73) Assignee: Ardea Biosciences, Inc., San Diego, CA (US)

(*) Notice: Subject to any disclaimer, the term of this patent is extended or adjusted under 35 U.S.C. 154(b) by 0 days.

(21) Appl. No.: 13/470,119

(22) Filed: May 11, 2012

(65) Prior Publication Data

US 2012/0225894 A1 Sep. 6, 2012

Related U.S. Application Data

(62) Division of application No. 12/504,566, filed on Jul. 16, 2009, now Pat. No. 8,211,898, which is a division of application No. 11/938,101, filed on Nov. 9, 2007, now Pat. No. 7,595,324.

(60) Provisional application No. 60/858,082, filed on Nov. 9, 2006.

(51) Int. Cl.
C07D 495/04 (2006.01)
A61K 31/519 (2006.01)
A61P 31/18 (2006.01)

(52) U.S. Cl. .................... 514/260.1; 544/278

(58) Field of Classification Search .............. 544/278; 514/260.1
See application file for complete search history.

(56) References Cited

U.S. PATENT DOCUMENTS

| 5,280,026 A | 1/1994 | Brown et al. |
| 6,197,779 B1 | 3/2001 | Andries et al. |
| 7,595,324 B2 | 9/2009 | Girardet et al. |
| 2004/0014755 A1 | 1/2004 | Nagarathnam et al. |

FOREIGN PATENT DOCUMENTS

| WO | WO-00-27850 A2 | 5/2000 |
| WO | WO-03-016306 A1 | 2/2003 |
| WO | WO-2004-069812 A1 | 8/2004 |
| WO | WO-2005-028479 A2 | 3/2005 |

OTHER PUBLICATIONS

Balzarni, J., "Current Status of the Non-nucleoside Reverse Transcriptase Inhibitors of Human Immunodeficiency Virus Type 1," Cur. Top. Med. Chem. 4:921-944 (2004).
Berge et al,, "Pharmaceutical salts," J. Pharm. Sci, 66(1): 1-19, 1977.
Buchwald et al., "Long-term, continuous intravenous heparin administration by an implantable infusion pump in ambulatory patients with recurrent venous thrombosis," Surgery 88(4): 507-16, 1980.
Bundgaard, H. Chapter 5: Design and application of prodrugs. A Textbook of Drug Design and Development. Krosgaard-Larsen, et al., eds., pp. 113-191, 1991.
Bundgaard, H., "Means to enhance penetration: Prodrugs as a means to improve the delivery of peptide drugs," Advanced Drug Delivery Reviews 8: 1-38, 1992.

Connor, R.I. et al., "Characterization of the Functional Properties of env Genes from Long-Term Survivors of Human Immunodeficiency Virus Type I Infection," J. Virol. 70:5306-5311 (1996).
Fedorak et al., "A novel colon-specific steroid prodrug enhances sodium chloride absorption in rat colitis," Am J Physiol 269(2 Pt 1): G210-8, 1995.
Fleisher et al., "Improved oral drug delivery: solubility limitations overcome by the use of prodrugs," Advanced Drug Delivery Reviews 19(2): 115-30, 1996.
Furniss et al., ed., Vogel's Textbook of Practical Organic Chemistry, 5th Ed. Suppl. (Longman Scientific and Technical Ltd, Essex, UK) pp. 809-16, 1991.
Goodson, J. Dental applications. Medical Applications of Controlled Release, vol. 2, Applications and Evaluations. Langer, et al., eds. (CRC Press, Boca Raton, FL) pp. 115-138, 1984.
Harrington, R. et al., "Direct detection of infectious HIV-1 in blood using a centrifugation-indicator cell assay," J.Virol. Methods 88:111-115 (2000).
Heller, A., "Electrical wiring of redox enzymes," Acc Chem Res 23(5): 128-84, 1990.
Hochhaus et al. A selective HPLC/RIA for dexamethasone and its prodrug dexamethasone-21-sulphobenzoate sodium in biological fluids. Biomed Chromatogr. 1992; 6(6):283-286 (1992).
Langer, R., "New methods of drug delivery," Science 249(4976): 1527-33, 1990. Larsen, et al., "Prodrug forms for the sulfonamide group. I. Evaluation of N-acyl derivative, N-sulfonylamidines, N-sulthnyisulfilimines and sulfonylureas as possible prodrug derivatives," Int J Pharmaceutics 37(1-2): 87-95, 1987.
Larsen et al., "Prodrug forms for the sulfonamide group. II. Water-soluble amino acid derivatives of N-methylsulfonamides as possible prodrugs," Int J. Pharmaceutics 47(1-3): 103-10, 1988.
Ludovici, D.W. et al, "Evolution of Anti-HIV Drug Candidates. Part 3. Diarylpyrimidine (DAPY) Analogues,"Bioorg. Med. Chem. Lett. 11:2235-2239 (2002).
McLeod et al., "A glucocorticoid prodrug facilitates normal mucosal function in rat colitis without adrenal suppression," Gastroenterology 106(2): 405-13, 1994.
Platt, E.J. et al., "Effects of CCR5 and CD4 Cell Surface Concentrations on Infections by Macrophagetropic Isolates of Human Immunodeficiency Virus Type 1," J. Virol. 73:2855-2864 (1998).
Popik, W. et al., "Human Immunodeficiency Virus Type 1 Uses Lipid Raft-Colocalized CD4 and Chemokine Receptors for Productive Entry into CD+ T Cells,"J. Virol. 76:4709-4722 (2002).
Robinson et al,. "Discovery of the hetnifutnarate and (alpha-L-alanyloxy)methyl ether as prodrugs of an antirheumatic oxindole: prodrugs for the enolic OH group," J Med Chem 39(1): 10-8, 1996.

(Continued)

Primary Examiner — Susanna Moore
(74) Attorney, Agent, or Firm — Wilson, Sonsini, Goodrich & Rosati

(57) ABSTRACT

This application concerns certain 4-cyanophenylamino-substituted bicyclic heterocycles of formula I

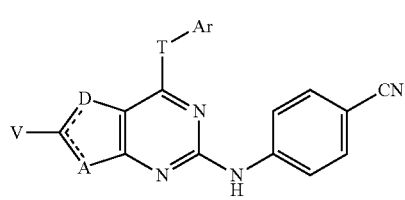

where the dashed line represents a double bond that may be located either between A and C(V) or between C(V) and D, where A is S or C(Z); D is S or C(W); provided that one and only one of A and D is S; where T is NH, O, or S; and where other substituents are defined herein. These compounds are non-nucleoside reverse transcriptase inhibitors and have potential as anti-HIV treatment.

46 Claims, No Drawings

OTHER PUBLICATIONS

Roos, J.W. et al., "LuSIV Cells: A Receptor Cell Line for the Detection and Quantitation of a Single Cycle of HIV and SIV Replication," Virology 273:307-315 (2000).

Saudek et al., "A preliminary trial of the programmable implantable medication system for insulin delivery," N Engl J Med 321(9): 574-9, 1989.

Saulnier et al., "An efficient method for the synthesis of guanidino prodrugs," Bioorganic & Medicinal Chemistry Letters 4(16): 1985-90, 1994.

Sefton, M., "Implantable pumps," Crit Rev Biomed Eng 14(3): 201-40, 1987.

Sinkula et al., "Rationale for design of biologically reversible drug derivatives: prodrugs," J Pharm Sci 64(2): 181-210, 1975.

Treat et al., "Liposome encapsulated doxorubicin: Preliminary results of phase 1 and phase II trials," Liposomes in the Therapy of Infectious Diseases and Cancer. Lopez-Bernstein, et al., eds. (Alan R. Liss, New York) pp. 353-365, 1989.

PCT/US07/84342 Search Report dated Sep. 12, 2008.

Notari, R.E., Chapter 24 "Theory and Practice of Prodrug Kinetics" from Widder's Methods in Enzymology, vol. 112:309-395 (1985).

Thayer, A.M., "Solid-State Services: Specialized companies help drug developers find crystalline forms with the right properties," Chem. Eng. News 85:31-34 (2007).

Vippagunta et al., "Crystalline solids," Advanced Drug Delivery Reviews 48:3-26 (2001).

SUBSTITUTED THIENO [2,3-D] PYRIMIDINES AS HIV INHIBITORS

CROSS-REFERENCE

This application is a divisional of a U.S. application Ser. No. 12/504,566, filed Jul. 16, 2009, now U.S. Pat. No. 8,211,898 which is a divisional of U.S. application Ser. No. 11/938,101, filed Nov. 9, 2007, which issued as U.S. Pat. No. 7,595,324 on Sep. 29, 2009, and which claims the benefit of U.S. Provisional Application No. 60/858,082, filed Nov. 9, 2006, each of which are incorporated herein by reference in their entirety.

BACKGROUND OF THE INVENTION

Human Immunodeficiency Virus (HIV) presents a public-health and social catastrophe too well known to require documentation. One therapeutic approach to HIV has been inhibition of the viral RNA-dependent RNA polymerase; this enzyme is frequently referred to as "reverse transcriptase," abbreviated "RT." The first RT inhibitors were nucleoside analogs such as AZT and ddI. Although such nucleoside RT inhibitors were frequently effective against the wild-type virus, any single-drug treatment has been hobbled by the virus's ability to readily produce drug-resistant mutants. This has lead to an intense search for non-nucleoside RT inhibitors ("NNRTIs"), which are both effective and capable of retaining their effectiveness despite drug-resistance mutations. A recent review of NNRTIs can be found in Balzarni, J., 2004, *Cur. Top. Med. Chem.* 4, 921-44 (Erratum ibid. 4, 1825).

Four leading NNRTI are: 1) Efavirenz (4S )-6-chloro-4-(cyclopropylethynyl)-1,4-dihydro-4-(trifluoromethyl)-2H-3,1-benzoxazin-2-one; 2) Capravirine: 1H-Imidazole-2-methanol, 5-((3,5-dichlorophenyl)thio)-4-(1-methylethyl)-1-(4-pyridinylmethyl)-carbamate (ester); 3) Etravirine (TMC 125): 4-((6-amino-5-bromo-2-((4-cyanophenyl)amino)-4-pyrimidinyl)oxy)-3,5-dimethyl-benzonitrile; and 4) Rilpivirine (TMC-278): 4-([4-[(4-[(/E)-2-cyanoethenyl]-2,6-dimethylphenyl)amino]-2- pyrimidinyl)amino]benzonitrile. Rilpivirine and Etravirine belong to a subclass of NNRTIs called diarylpyrmidines ("DAPY"). For a review of these DAPY NNRTIs see Ludovici, D. W., et al., 2002, *Bioorg. Med. Chem. Lett.* 11, 2235-9. An extensive patent literature also exists for DAPY. U.S. Pat. No. 6,197,779; WO 00/27850; WO 2003/016306; and WO 2004/069812, all of which are assigned to Janssen Pharmaceuticals.

Diaryl compounds similar to Etravirine and Rilpivirine where the pyrimidine moiety is replaced by a purine are described in WO 2005/028479, which also is assigned to Janssen.

SUMMARY OF THE INVENTION

The invention provides compounds of formula I:

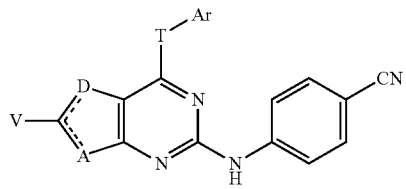

where the dashed line represents a double bond that may be located either between A and C(V) or between C(V) and D;
A is S or C(Z);
D is S or C(W);
provided that one and only one of A and D is S;
T is NH, O, or S;
W and Z are, independently, H, F, Cl, Br, $C_1$-$C_6$ alkyl; $C_2$-$C_6$ alkenyl; $OC_1$-$C_6$ alkyl; $C_3$-$C_6$ cycloalkyl; $OC_3$-$C_6$ cycloalkyl, phenyl, or benzyl, wherein alkyl, alkenyl, cycloalkyl, and phenyl groups and the phenyl moiety of the benzyl group are optionally substituted with 1-3 groups selected from halogen, $CF_3$, $C_1$-$C_3$ alkyl, and $OC_1$-$C_3$ alkyl
V is H, halogen, $C_1$-$C_6$ alkyl;
or V and W, together with the ring atoms to which they are attached, form an additional, fused 5-, 6-, or 7-membered ring, optionally containing one or two heteroatoms, which additional ring may be saturated, unsaturated, or aromatic;
or V and Z, together with the ring atoms to which they are attached, form an additional, fused 5-, 6-, or 7-membered ring, optionally containing one or two heteroatoms, which additional ring may be saturated, unsaturated, or aromatic;
Ar is selected from (a), (b), (c), and (d) below:

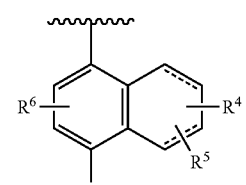

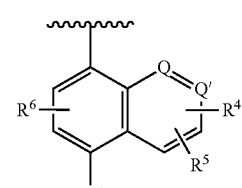

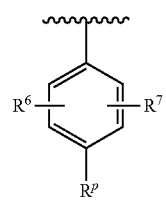

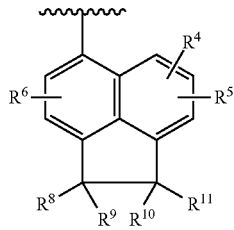

wherein
each $R^P$ is selected from among methyl, ethyl, propyl, isopropyl, cyclopropylmethyl, or $C_3$-$C_6$ cycloalkyl, cyano, CH=CHCN, Cl, Br, I, acetyl, and $C_1$-$C_6$ alkyl-NH;
$R^4$, $R^5$ and each $R^6$ are independently selected from H, F, Cl, Br, $CH_3$, $CF_3$, $CH_2F$, $CHF_2$, isopropyl, cyclopropyl, $OCH_3$, OH, $OCF_3$, $NH_2$, and $NHCH_3$, or $R^6$ and $R^P$ on adjacent ring atoms, together with the ring atoms to which they are attached, form an additional fused five-membered ring;

Q and Q' are independently selected from N and CH;

$R^7$ is Cl, Br, I, $CH_3$, $CF_3$, $OCH_3$, isopropyl, cyclopropyl, t-butyl, or cyclobutyl; and $R^8$-$R^{11}$ are, independently, H or $CH_3$;

or a pharmaceutically acceptable salt, solvate, hydrate, polymorph, ester., tautomer or prodrug thereof.

In one generic embodiment this invention provides a compound of formula IA, in which the 6-linker T in formula I is T', which may be O or S.

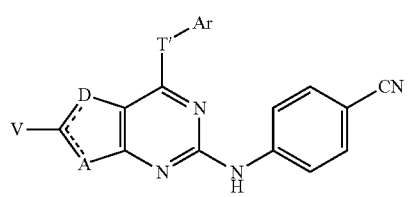

IA

In one subgeneric embodiment, the invention provides or contemplates a compound of formula IA where Ar is selected from 2-chloro-4-cyclopropyl phenyl; 2-methyl-4-cyclopropyl-naphth-1-yl; 2,6-dimethyl-4-cyanophenyl; 2,6-dimethoxy-4-cyanophenyl; 2,6-dimethyl-4-(2-cyanoethenyl) phenyl; 2,6-dimethoxy-4-(2-cyanoethenyl) phenyl; 2-methyl-4-cyclopropyl phenyl; 2,6-dimethyl-4-cyclopropyl phenyl; 2,6-di-trifluoromethyl-4-cyclopropyl phenyl; 2,4,6-trimethyl phenyl; and 2,6-dimethyl-4-acetyl phenyl.

In another subgeneric embodiment, the invention contemplates a compound of formula IA where Ar is selected from the following: 5-cyclopropyl-8-quinolyl; 5-isopropyl-8-quinolyl; 5-cyano-8-quinolyl; 5-cyclopropyl-7-trifluoromethyl-8-quinolyl; 5-acetyl-8-quinolyl; 5-cyano-7-methoxy-8-quinolyl; 5-cyano-7-methyl-8-quinolyl; 5-cyclopropyl-7-trifluoromethoxy-8-isoquinolyl; 5-cyano-8-isoquinolyl; 5-cyano-7-methoxy-8-isoquinolyl; 5-cyano-7-methyl-8-isoquinolyl; 5-cyclobutyl-7-difluoromethyl-8-isoquinolyl; 5,7-dimethyl-8-cinnolyl; 5-cyclopropyl-7-methyl-8-cinnolyl; and 5-(2-cyanoethenyl)-7-methyl-8-cinnolyl.

In another subgeneric embodiment, the invention provides a compound of formula IA-1

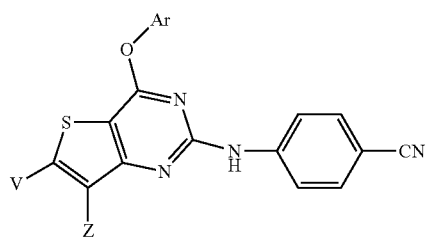

IA-1 where Ar, V, and Z are defined as for formula I.

In another subgeneric embodiment, the invention provides a compound of formula IA-2

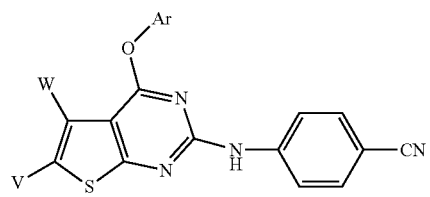

IA-2 where Ar, V, and W are defined as for formula I.

In another subgeneric embodiment, this invention provides a compound of formula IA-3

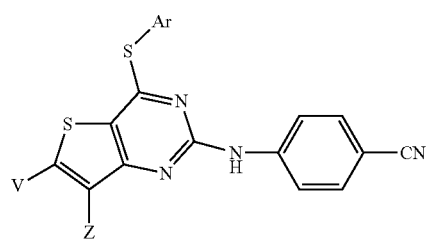

IA-3 where Ar, V and Z are defined as for formula I.

In another subgeneric embodiment, this invention provides a compound of formula IA-4

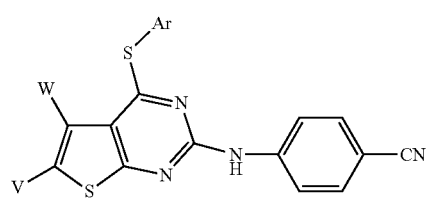

IA-4 where Ar, V and W are defined as for formula I.

In another generic embodiment, this invention provides a compound of formula IB

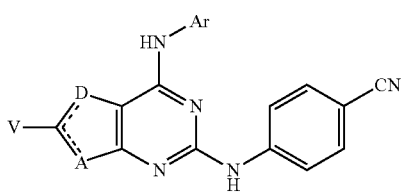

IB where all substituents are as described above.

In one subgeneric embodiment, the invention provides a compound of formula IB where Ar is (c).

In a more specific subgeneric embodiment, the invention provides a compound of formula IB where Ar is

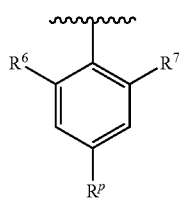

where RP is CN, CH=CHCN, or cyclopropyl; where $R^6$ and $R^7$ are either both methyl or both methoxy.

In another subgeneric embodiment, this invention provides a compound of formula IB-1.

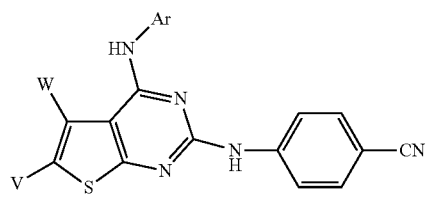

IB-1 where Ar, V and W are defined as for formula I.

In another subgeneric embodiment, this invention provides a compound of formula IB-2.

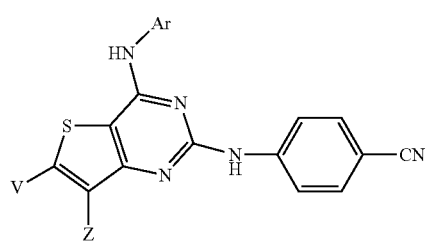

IB-2 where Ar, V and Z are as described above for formula I.

In more specific embodiments, the invention provides compounds of any of IA-1, IA-2, IA-3, IA-4, IB-1, IB-2, where Ar is (a).

In additional more specific embodiments, the invention provides compounds of any of IA-1, IA-2, IA-3, IA-4, IB-1, IB-2, where Ar is (b).

In additional more specific embodiments, the invention provides compounds of any of IA-1, IA-2, IA-3, IA-4, IB-1, IB-2, where Ar is (c).

In additional more specific embodiments, the invention provides compounds of any of IA-1, IA-2, IA-3, IA-4, IB-1, IB-2, where Ar is (d).

In another more specific subgeneric embodiment, this invention provides or contemplates a compound of formula IA-1, IA-2, IA-3, or IA-4, where Ar is 2,6-disubstituted-4-cyclopropyl, 2,6-disubstituted-4-acetyl, 2,4,6-trimethyl, 2,6-disubstituted-4-bromo, or 4-cyano-2,6-di-substituted phenyl.

In a still more specific subgeneric embodiment, this invention provides or contemplates compounds of formula IA-1, IA-2, IA-3, or IA-4, where Ar is 4-cyano-2,6-di-methoxy phenyl or 4-cyano-2,6-di-methyl phenyl.

In another still more specific subgeneric embodiment, this invention provides or contemplates compounds of formula IA-1, IA-2, IA-3, or IA-4, where V is H, halo, or methyl.

In another still more specific subgeneric embodiment, this invention provides or contemplates compounds of formula IA-1, IA-2, IA-3, or IA-4, where A is S and W is H, phenyl, or benzyl.

In another still more specific subgeneric embodiment, this invention provides or contemplates a compound of formula IA-1, IA-2, IA-3, or IA-4, where A is S and W is H, $C_3$-$C_6$ cycloalkyl, or $OC_3$-$C_6$ cycloalkyl.

In another still more specific subgeneric embodiment, this invention provides or contemplates compounds of formula IA-1, IA-2, IA-3, or IA-4, where A is S and W is H, unsubstituted $C_1$-$C_4$ alkyl, monosubstituted $C_1$-$C_4$ alkyl, or $C_2$-$C_3$ alkenyl.

In another still more specific subgeneric embodiment, this invention provides or contemplates compounds of formula IA-1, IA-2, IA-3, or IA-4, where A is S and W is H, halo, halomethyl, or methyl.

In another still more specific subgeneric embodiment, this invention provides or contemplates compounds of formula IA-1, IA-2, IA-3, or IA-4, where A is S and V and W, together with the ring atoms to which they are attached, form an additional, fused 5-, 6-, or 7-membered carbocyclic ring.

In another still more specific subgeneric embodiment, this invention provides or contemplates compounds of formula IA-1, IA-2, IA-3, or IA-4, where A is S and V and W, together with the ring atoms to which they are attached, form an additional, fused 5-, 6-, or 7- membered ring, which ring contains one or two heteroatoms selected from O, N, and S.

In another still more specific subgeneric embodiment, this invention provides or contemplates compounds of formula IA-1, IA-2, IA-3, or IA-4, where D is S and Z is H, $C_1$-$C_6$ alkyl, or $C_2$-$C_6$ alkenyl.

In another still more specific subgeneric embodiment, this invention provides or contemplates compounds of formula IA-1, IA-2, IA-3, or IA-4, where D is S and Z is H, $C_3$-$C_6$ cycloalkyl, or $OC_3$-$C_6$ cycloalkyl.

In another still more specific subgeneric embodiment, this invention provides or contemplates compounds of formula IA-1, IA-2, IA-3, or IA-4, where D is S and Z is H, unsubstituted $C_1$-$C_4$ alkyl, monosubstituted $C_1$-$C_4$ alkyl, or $C_2$-$C_3$ alkenyl.

In another still more specific subgeneric embodiment, this invention provides or contemplates compounds of formula IA-1, IA-2, IA-3, or IA-4, where D is S and Z is H, halo, halomethyl, or methyl.

In another still more specific subgeneric embodiment, this invention provides or contemplates a compound of formula IA-1, IA-2, IA-3, or IA-4, where D is S and Z is H, phenyl, or benzyl.

In another still more specific subgeneric embodiment, this invention provides or contemplates compounds of formula IA-1, IA-2, IA-3, or IA-4, where D is S and V and Z, together with the ring atoms to which they are attached, form an additional, fused 5-, 6-, or 7- membered carbocyclic ring.

In another still more specific subgeneric embodiment, this invention provides or contemplates compounds of formula IA-1, IA-2, IA-3, or IA-4, where D is S and V and Z, together with the ring atoms to which they are attached, form an additional, fused 5-, 6-, or 7-membered ring, which ring contains one or two heteroatoms selected from O, N, and S.

In a preferred embodiment, the invention provides for compounds of formula I and their pharmaceutically acceptable salts.

In further or additional embodiments, the invention provides for compounds of formula I and their pharmaceutically acceptable solvates.

In further or additional embodiments, the invention provides for compounds of formula I and their pharmaceutically acceptable hydrates.

In further or additional embodiments, the invention provides for compounds of formula I and their pharmaceutically acceptable polymorphs.

In further or additional embodiments, the invention provides for compounds of formula I and their pharmaceutically acceptable esters.

In further or additional embodiments, the invention provides for compounds of formula I and their pharmaceutically acceptable tautomers.

In further or additional embodiments, the invention provides for compounds of formula I and their pharmaceutically acceptable prodrugs.

The compounds described herein have inhibitory activity against both wild-type and mutated forms of human immunodeficiency virus type 1 (HIV-1).

Described herein are pharmaceutical compositions comprising a compound of formula I or a pharmaceutically acceptable salt, solvate, polymorph, ester, tautomer or prodrug thereof. In some embodiments, the pharmaceutical compositions further comprise a pharmaceutically acceptable carrier. Such compositions may contain adjuvants, excipients, preservatives, agents for delaying absorption, fillers, binders, adsorbents, buffers, disintegrating agents, solubilizing agents, other carriers, and other inert ingredients. Methods of formulation of such compositions are well-known in the art.

In some embodiments, the pharmaceutical composition is in a form suitable for oral administration. In further or additional embodiments, the pharmaceutical composition is in the form of a tablet, capsule, pill, powder, sustained release formulation, solution, suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.002 to about 6 g/day. In further or additional embodiments the amount of compound of formula I is about 0.005 to about 5 g/day. In further or additional embodiments the amount of compound of formula I is about 0.01 to about 5 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the pharmaceutical composition is for administration to a mammal. In further or additional embodiments, the mammal is human. In further or additional embodiments, the pharmaceutical composition further comprises a pharmaceutical carrier, excipient and/or adjuvant. In further or additional embodiments, the pharmaceutical composition further comprises at least one therapeutic agent In further or additional embodiments, the therapeutic agent is an HIV or AIDS drug, or a drug for the treatment of the symptoms of HIV or AIDS. . In further or additional embodiments, the pharmaceutical composition is administered in combination with an additional therapy. In further or additional embodiments, the pharmaceutical composition comprises a pharmaceutically acceptable salt of a compound of formula I.

Also described herein are methods for inhibiting a reverse transcriptase enzyme. In some embodiments, the method comprises contacting said reverse transcriptase enzyme with an amount of a composition comprising a compound of formula I or a pharmaceutically acceptable salt, solvate, polymorph, ester, tautomer or prodrug thereof, sufficient to inhibit said enzyme, wherein said enzyme is inhibited. In further or additional embodiments the enzyme is at least about 1% inhibited. In further or additional embodiments the enzyme is at least about 2% inhibited. In further or additional embodiments the enzyme is at least about 3% inhibited. In further or additional embodiments the enzyme is at least about 4% inhibited. In further or additional embodiments the enzyme is at least about 5% inhibited. In further or additional embodiments the enzyme is at least about 10% inhibited. In further or additional embodiments the enzyme is at least about 20% inhibited. In further or additional embodiments the enzyme is at least about 25% inhibited. In further or additional embodiments the enzyme is at least about 30% inhibited. In further or additional embodiments the enzyme is at least about 40% inhibited. In further or additional embodiments the enzyme is at least about 50% inhibited. In further or additional embodiments the enzyme is at least about 60% inhibited. In further or additional embodiments the enzyme is at least about 70% inhibited. In further or additional embodiments the enzyme is at least about 75% inhibited. In further or additional embodiments the enzyme is at least about 80% inhibited. In further or additional embodiments the enzyme is at least about 90% inhibited. In further or additional embodiments the enzyme is essentially completely inhibited. In further or additional embodiments the reverse transcriptase enzyme is HIV reverse transcriptase. In further or additional embodiments the reverse transcriptase enzyme is HIV-1 reverse transcriptase. In further or additional embodiments the HIV reverse transcriptase is resistant to non-nucleoside reverse transcriptase inhibitors. In further or additional embodiments the contacting occurs within a cell. In further or additional embodiments the cell is a mammalian cell. In further or additional embodiments the mammalian cell is a human cell. In further or additional embodiments the contacting occurs in vitro. In further or additional embodiments the contacting occurs in vivo. In further or additional embodiments the contacting occurs within the body of a subject infected with HIV. In further or additional embodiments, the reverse transcriptase enzyme is inhibited with a composition comprising a pharmaceutically acceptable salt of a compound of formula I.

Also described herein are methods of treating or preventing a disease in an individual comprising administering to said individual an effective amount of a compound of formula I or a composition comprising a compound of formula I or a pharmaceutically acceptable salt, solvate, polymorph, ester, tautomer or prodrug thereof. In further or additional embodiments, the disease is HIV. In further or additional embodiments, the disease is AIDS. In further or additional embodiments, the disease is ARC.

Also described herein are compounds that inhibit the replication of HIV, including drug resistant strains of the virus. Accordingly, the present invention provides pharmaceutical compositions, and prophylactic and therapeutic treatments, diagnostic and prognostic methods and kits, and pharmaceutical screening methods that take advantage of the anti-HIV activity of these compounds and compositions. Compounds that inhibit HIV replication are candidates for the prophylactic or therapeutic treatment of HIV infection. Prophylactic treatments are especially useful for persons at high risk of HIV infection.

Also described herein are compositions comprising at least one compound of formula I and a second therapeutic agent or agents. In some embodiments, the second therapeutic agent is used to prevent or treat HIV infection. In further or additional embodiments, the second therapeutic agent is used to treat an opportunistic infection associated with HIV infection. The second therapeutic is, for example, a protease inhibitor, a non-nucleoside reverse transcriptase inhibitor, a nucleoside reverse transcriptase inhibitor, an antiretroviral nucleoside, an entry inhibitor, or any other anti-viral agent effective to inhibit or treat HIV infection. In further or additional embodiments, the second therapeutic agent is selected from the group consisting of zidovudine, didanosine, stavudine, interferon, lamivudine, adefovir, nevirapine, delaviridine, loviride, saquinavir, indinavir, and AZT. In further or additional embodiments, the second therapeutic agent is an antibiotic or acyclovir. In still a further embodiment, the second agent is selected from immunomodulators, and entry inhibitors.

Also described herein are methods of inhibiting HW replication in a person by administering to the person a pharmaceutically effective amount of at least one compound of formula I. Further described herein are methods of treating or preventing HIV infection in a subject comprising administering compound of formula I to a subject. The compounds described herein can be administered orally, parentally (including subcutaneous injection, intravenous, intramuscular, intrasternal or infusion techniques), by inhalation spray, topically, by absorption through a mucous membrane, or rectally, in dosage unit formulations containing conventional nontoxic pharmaceutically acceptable carriers, adjuvants or vehicles.

Also described herein are methods for inhibiting the replication of drug resistant, including multi-drug resistant, HIV mutants, comprising administering at least one compound of formula I. The compounds of the invention are potent against HIV and drug resistant strains of HW.

In another aspect, the present invention provides methods of inhibiting HIV infection in a CD4 culture comprising contacting the cell at least one compound of formula I, either alone or in combination with a second therapeutic agent or a combination of other therapeutic agents. In some embodiments, the therapeutic agent or agents are used to treat or prevent HIV infection.

The present invention provides new compositions and methods for preventing or ameliorating viral, e.g., HW infection, killing virally infected cells, e.g., HW infected cells and generally, inhibiting viral, preferably HIV, replication. The compounds described herein effectively inhibit HIV infection, kill HIV infected cells and/or prevent HIV infection in the individual. Moreover, the compounds of the invention inhibit the replication of drug resistant strains of HIV.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Certain Chemical Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting.

Definition of standard chemistry terms may be found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, —$CH_2O$— is equivalent to —$OCH_2$—.

Unless otherwise noted, the use of general chemical terms, such as though not limited to "alkyl," "amine," "aryl," are equivalent to their optionally substituted forms. For example, "alkyl," as used herein, includes optionally substituted alkyl.

The compounds presented herein may possess one or more stereocenters and each center may exist in the R or S configuration, or combinations thereof. Likewise, the compounds presented herein may possess one or more double bonds and each may exist in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. Techniques for inverting or leaving unchanged a particular stereocenter, and those for resolving mixtures of stereoisomers are well known in the art and it is well within the ability of one of skill in the art to choose an appropriate method for a particular situation. See, for example, Furniss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, *Acc. Chem. Res.* 1990, 23, 128.

The terms "moiety", "chemical moiety", "group" and "chemical group", as used herein refer to a specific segment or functional group of a molecule. Chemical moieties are often recognized chemical entities embedded in or appended to a molecule.

The term "bond" or "single bond" refers to a chemical bond between two atoms, or two moieties when the atoms joined by the bond are considered to be part of larger substructure.

The term "catalytic group" refers to a chemical functional group that assists catalysis by acting to lower the activation barrier to reaction.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, an optionally substituted group may be un-substituted (e.g., —$CH_2CH_3$), fully substituted (e.g., —$CF_2CF_3$), mono-substituted (e.g., —$CH_2CH_2F$) or substituted at a level anywhere in-between fully substituted and mono-substituted (e.g., —$CH_2CHF_2$, —$CH_2CF_3$, —$CF_2CH_3$, —$CFHCHF_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The term "hydrocarbon" as used herein, alone or in combination, refers to a compound or chemical group containing only carbon and hydrogen atoms.

The terms "heteroatom" or "hetero" as used herein, alone or in combination, refer to an atom other than carbon or hydrogen. Heteroatoms are may be independently selected from among oxygen, nitrogen, sulfur, phosphorous, silicon, selenium and tin but are not limited to these atoms. In embodiments in which two or more heteroatoms are present, the two or more heteroatoms can be the same as each another, or some or all of the two or more heteroatoms can each be different from the others.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The term "alkylene" as used herein, alone or in combination, refers to a diradical derived from the above-defined monoradical, alkyl. Examples include, but are not limited to methylene (—$CH_2$—), ethylene (—$CH_2CH_2$—), propylene (—$CH_2CH_2CH_2$—), isopropylene (—$CH(CH_3)CH_2$—) and the like.

The term "alkenyl" as used herein, alone or in combination, refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "C$_2$-C$_6$ alkenyl" or "C$_{2-6}$ alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated.

The term "alkenylene" as used herein, alone or in combination, refers to a diradical derived from the above-defined monoradical alkenyl. Examples include, but are not limited to ethenylene (—CH=CH—), the propenylene isomers (e.g., —CH$_2$CH=CH— and —C(CH$_3$)=CH—) and the like.

The term "alkynyl" as used herein, alone or in combination, refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "C$_2$-C$_6$ alkynyl" or "C$_{2-6}$ alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated.

The term "alkynylene" as used herein, alone or in combination, refers to a diradical derived from the above-defined monoradical, alkynyl. Examples include, but are not limited to ethynylene (—C≡C—), propargylene (—CH$_2$—C≡C—) and the like.

The term "aliphatic" as used herein, alone or in combination, refers to an optionally substituted, straight-chain or branched-chain, non-cyclic, saturated, partially unsaturated, or fully unsaturated nonaromatic hydrocarbon. Thus, the term collectively includes alkyl, alkenyl and alkynyl groups.

The terms "heteroalkyl", "heteroalkenyl" and "heteroalkynyl" as used herein, alone or in combination, refer to optionally substituted alkyl, alkenyl and alkynyl structures respectively, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof), or heteroatomic group such as though not limited to —O—O—, —S—S—, —O—S—, —S—O—, =N—N=, —N=N—, —N=N—NH—, —P(O)$_2$—, —O—P(O)$_2$—, —P(O)$_2$—O—, —S(O)—, —S(O)$_2$—, —SnH$_2$— and the like.

The terms "haloalkyl", "haloalkenyl" and "haloalkynyl" as used herein, alone or in combination, refer to optionally substituted alkyl, alkenyl and alkynyl groups respectively, as defined above, in which one or more hydrogen atoms is replaced by fluorine, chlorine, bromine or iodine atoms, or combinations thereof. In some embodiments two or more hydrogen atoms may be replaced with halogen atoms that are the same as each another (e.g. difluoromethyl); in other embodiments two or more hydrogen atoms may be replaced with halogen atoms that are not all the same as each other (e.g. 1-chloro-1-fluoro-1-iodoethyl). Non-limiting examples of haloalkyl groups are fluoromethyl and bromoethyl. A non-limiting example of a haloalkenyl group is bromoethenyl. A non-limiting example of a haloalkynyl group is chloroethynyl.

The term "perhalo" as used herein, alone or in combination, refers to groups in which all of the hydrogen atoms are replaced by fluorines, chlorines, bromines, iodines, or combinations thereof. Thus, as a non-limiting example, the term "perhaloalkyl" refers to an alkyl group, as defined herein, in which all of the H atoms have been replaced by fluorines, chlorines, bromines or iodines, or combinations thereof. A non-limiting example of a perhaloalkyl group is bromo,chloro,fluoromethyl. A non-limiting example of a perhaloalkenyl group is trichloroethenyl. A non-limiting example of a perhaloalkynyl group is tribromopropynyl.

The term "carbon chain" as used herein, alone or in combination, refers to any alkyl, alkenyl, alkynyl, heteroalkyl, heteroalkenyl or heteroalkynyl group, which is linear, cyclic, or any combination thereof. If the chain is part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining the chain length. If the chain contains heteroatoms as part of the backbone, those atoms are not calculated as part of the carbon chain length.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. Rings can be optionally substituted. Rings can form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "fused" as used herein, alone or in combination, refers to cyclic structures in which two or more rings share one or more bonds.

The term "cycloalkyl" as used herein, alone or in combination, refers to an optionally substituted, saturated, hydrocarbon monoradical ring, containing from three to about fifteen ring carbon atoms or from three to about ten ring carbon atoms, though may include additional, non-ring carbon atoms as substituents (e.g. methylcyclopropyl). Whenever it appears herein, a numerical range such as "C$_3$-C$_6$ cycloalkyl" or "C$_{3-6}$ cycloalkyl", means that the cycloalkyl group may consist of 3 carbon atoms, 4 carbon atoms, 5 carbon atoms or 6 carbon atoms, i.e., is cyclopropyl, cyclobutyl, cyclopentyl or cyclohepty, although the present definition also covers the occurrence of the term "cycloalkyl" where no numerical range is designated. The term includes fused, non-fused, bridged and spiro radicals. A fused cycloalkyl may contain from two to four fused rings where the ring of attachment is a cycloalkyl ring, and the other individual rings may be alicyclic, heterocyclic, aromatic, heteroaromatic or any combination thereof. Examples include, but are not limited to cyclopropyl, cyclopentyl, cyclohexyl, decalinyl, and bicyclo [2.2.1] heptyl and adamantyl ring systems. Illustrative examples include, but are not limited to the following moieties:

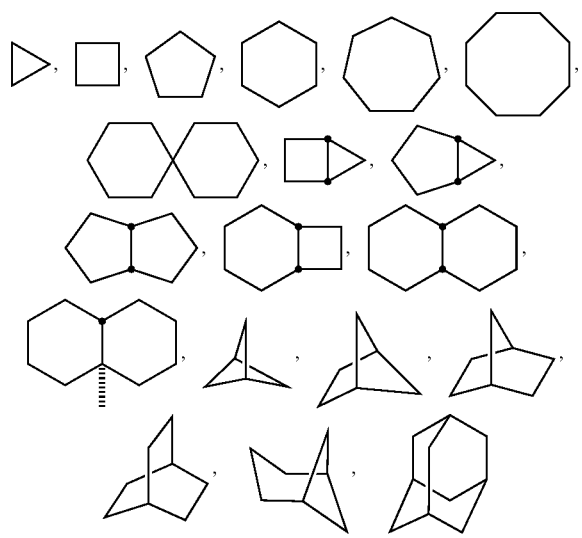

and the like.

The term "cycloalkenyl" as used herein, alone or in combination, refers to an optionally substituted hydrocarbon non-aromatic, monoradical ring, having one or more carbon-carbon double-bonds and from three to about twenty ring carbon atoms, three to about twelve ring carbon atoms, or from three to about ten ring carbon atoms. The term includes fused, non-fused, bridged and spiro radicals. A fused cycloalkenyl may contain from two to four fused rings where the ring of attachment is a cycloalkenyl ring, and the other individual rings may be alicyclic, heterocyclic, aromatic, heteroaromatic or any combination thereof. Fused ring systems may be fused across a bond that is a carbon-carbon single bond or a carbon-carbon double bond. Examples of cycloalkenyls include, but are not limited to cyclohexenyl, cyclopentadienyl and bicyclo[2.2.1]hept-2-ene ring systems. Illustrative examples include, but are not limited to the following moieties:

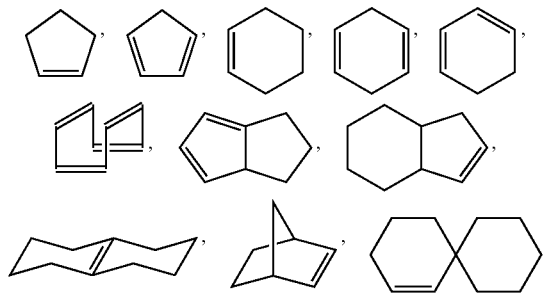

and the like.

The terms "alicyclyl" or "alicyclic" as used herein, alone or in combination, refer to an optionally substituted, saturated, partially unsaturated, or fully unsaturated nonaromatic hydrocarbon ring systems containing from three to about twenty ring carbon atoms, three to about twelve ring carbon atoms, or from three to about ten ring carbon atoms. Thus, the terms collectively include cycloalkyl and cycloalkenyl groups.

The terms "non-aromatic heterocyclyl" and "heteroalicyclyl" as used herein, alone or in combination, refer to optionally substituted, saturated, partially unsaturated, or fully unsaturated nonaromatic ring monoradicals containing from three to about twenty ring atoms, where one or more of the ring atoms are an atom other than carbon, independently selected from among oxygen, nitrogen, sulfur, phosphorous, silicon, selenium and tin but are not limited to these atoms. In embodiments in which two or more heteroatoms are present in the ring, the two or more heteroatoms can be the same as each another, or some or all of the two or more heteroatoms can each be different from the others. The terms include fused, non-fused, bridged and spiro radicals. A fused non-aromatic heterocyclic radical may contain from two to four fused rings where the attaching ring is a non-aromatic heterocycle, and the other individual rings may be alicyclic, heterocyclic, aromatic, heteroaromatic or any combination thereof. Fused ring systems may be fused across a single bond or a double bond, as well as across bonds that are carbon-carbon, carbon-hetero atom or hetero atom-hetero atom. The terms also include radicals having from three to about twelve skeletal ring atoms, as well as those having from three to about ten skeletal ring atoms. Attachment of a non-aromatic heterocyclic subunit to its parent molecule can be via a heteroatom or a carbon atom. Likewise, additional substitution can be via a heteroatom or a carbon atom. As a non-limiting example, an imidazolidine non-aromatic heterocycle may be attached to a parent molecule via either of its N atoms (imidazolidin-1-yl or imidazolidin-3-yl) or any of its carbon atoms (imidazolidin-2-yl, imidazolidin-4-yl or imidazolidin-5-yl). In certain embodiments, non-aromatic heterocycles contain one or more carbonyl or thiocarbonyl groups such as, for example, oxo- and thio-containing groups. Examples include, but are not limited to pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Illustrative examples of heterocycloalkyl groups, also referred to as non-aromatic heterocycles, include:

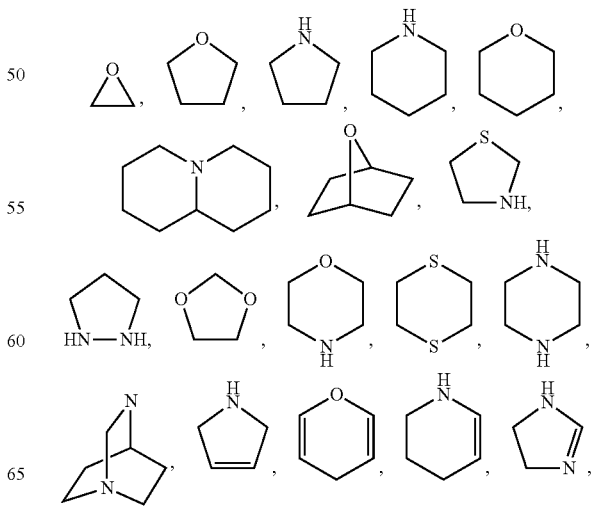

and the like. The terms also include all ring forms of the carbohydrates, including but not limited to the monosaccharides, the disaccharides and the oligosaccharides.

The term "aromatic" as used herein, refers to a planar, cyclic or polycyclic, ring moiety having a delocalized π-electron system containing 4n+2π electrons, where n is an integer. Aromatic rings can be formed by five, six, seven, eight, nine, or more than nine atoms. Aromatics can be optionally substituted and can be monocyclic or fused-ring polycyclic. The term aromatic encompasses both all carbon containing rings (e.g., phenyl) and those rings containing one or more heteroatoms (e.g., pyridine).

The term "aryl" as used herein, alone or in combination, refers to an optionally substituted aromatic hydrocarbon radical of six to about twenty ring carbon atoms, and includes fused and non-fused aryl rings. A fused aryl ring radical contains from two to four fused rings where the ring of attachment is an aryl ring, and the other individual rings may be alicyclic, heterocyclic, aromatic, heteroaromatic or any combination thereof. Further, the term aryl includes fused and non-fused rings containing from six to about twelve ring carbon atoms, as well as those containing from six to about ten ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl.

The term "arylene" as used herein, alone or in combination, refers to a diradical derived from the above-defined monoradical, aryl. Examples include, but are not limited to 1,2-phenylene, 1,3-phenylene, 1,4-phenylene, 1,2-naphthylene and the like.

The term "heteroaryl" as used herein, alone or in combination, refers to optionally substituted aromatic monoradicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidiazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazinyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide. Illustrative examples of heteroaryl groups include the following moieties:

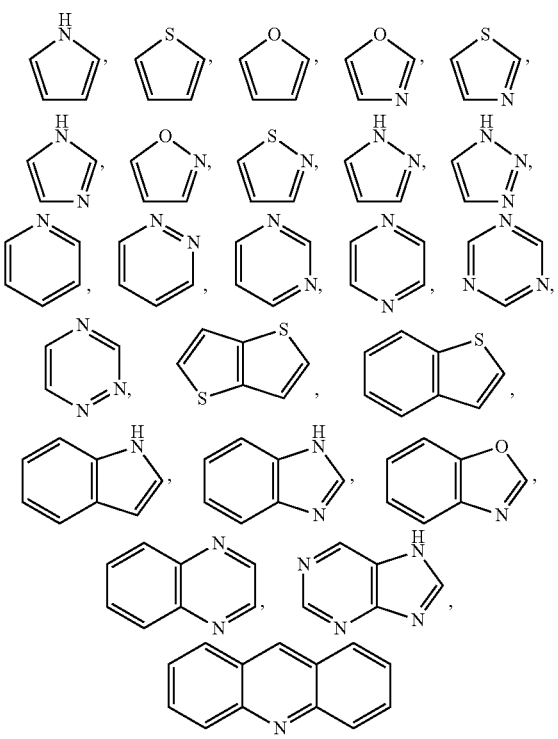

and the like.

The term "heteroarylene" as used herein, alone or in combination, refers to a diradical derived from the above-defined monoradical heteroaryl. Examples include, but are not limited to pyridinyl and pyrimidinyl.

The term "heterocyclyl" as used herein, alone or in combination, refers collectively to heteroalicyclyl and heteroaryl groups. Herein, whenever the number of carbon atoms in a heterocycle is indicated (e.g., $C_1$-$C_6$ heterocycle), at least one non-carbon atom (the heteroatom) must be present in the ring. Designations such as "$C_1$-$C_6$ heterocycle" refer only to the number of carbon atoms in the ring and do not refer to the total number of atoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). For heterocycles having two or more heteroatoms, those two or more heteroatoms can be the same or different from one another. Heterocycles can be optionally substituted. Non-aromatic heterocyclic groups include groups having only three atoms in the ring, while aromatic heterocyclic groups must have at least five atoms in the ring. Bonding (i.e. attachment to a parent molecule or further substitution) to a heterocycle can be via a heteroatom or a carbon atom.

The term "carbocyclyl" as used herein, alone or in combination, refers collectively to alicyclyl and aryl groups; i.e. all carbon, covalently closed ring structures, which may be saturated, partially unsaturated, fully unsaturated or aromatic. Carbocyclic rings can be formed by three, four, five, six, seven, eight, nine, or more than nine carbon atoms. Carbocycles can be optionally substituted. The term distinguishes carbocyclic from heterocyclic rings in which the ring backbone contains at least one atom which is different from carbon.

The terms "halogen", "halo" or "halide" as used herein, alone or in combination refer to fluoro, chloro, bromo and iodo.

The term "hydroxy" as used herein, alone or in combination, refers to the monoradical —OH.

The term "cyano" as used herein, alone or in combination, refers to the monoradical —CN.

The term "cyanomethyl" as used herein, alone or in combination, refers to the monoradical —$CH_2CN$.

The term "nitro" as used herein, alone or in combination, refers to the monoradical —$NO_2$.

The term "oxy" as used herein, alone or in combination, refers to the diradical —O—.

The term "oxo" as used herein, alone or in combination, refers to the diradical =O.

The term "carbonyl" as used herein, alone or in combination, refers to the diradical —C(=O)—, which may also be written as —C(O)—.

The terms "carboxy" or "carboxyl" as used herein, alone or in combination, refer to the moiety —C(O)OH, which may also be written as —COOH.

The term "alkoxy" as used herein, alone or in combination, refers to an alkyl ether radical, —O-alkyl, including the groups —O-aliphatic and —O-carbocyclyl, wherein the alkyl, aliphatic and carbocyclyl groups may be optionally substituted, and wherein the terms alkyl, aliphatic and carbocyclyl are as defined herein. Non-limiting examples of alkoxy radicals include methoxy, ethoxy, n-propoxy, isopropoxy, n-butoxy, iso-butoxy, sec-butoxy, tert-butoxy and the like.

The term "reactant," as used herein, refers to a nucleophile or electrophile used to create covalent linkages.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

Certain Pharmaceutical Terminology

The term "subject", "patient" or "individual" as used herein in reference to individuals suffering from a disorder, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

A "disorder associated with HIV infection" or "disease associated with HIV infection" refers to a disease state which is marked by HW infection. Such disorders associated with HIV infection include, but are not limited to, AIDS, Kaposi's sarcoma, opportunistic infections such as those caused by Pneumocystis carinii and Mycobacterium tuberculosis; oral lesions, including thrush, hairy leukoplakia, and aphthous ulcers; generalized lymphadenopathy, shingles, thrombocytopenia, aseptic meningitis, and neurologic disease such as toxoplasmosis, cryptococcosis, CMV infection, primary CNS lymphoma, and HIV-associated dementia, peripheral neuropathies, seizures, and myopathy.

As used herein, a compound that "inhibits replication of human immunodeficiency virus (HIV)" means a compound that, when contacted with HIV, for example, via HIV-infected cells, effects a reduction in the amount of HIV as compared with untreated control Inhibition of replication of HIV can be measured by various means known in the art, for example, the p24 assay.

The term "Mutant HIV" as used herein refers to a strain of HIV having one or more mutated or altered amino acids as compared with wild type.

The term "Multi-Drug Resistant HIV" as used herein refers to one or more HIV strains that are resistant to treatment with one or more chemotherapeutic agents.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical Sciences (current edition), Mack Publishing Co., Easton, Pa. In preferred embodiments, the compounds and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively nontoxic chemical compounds or agents that facilitate the incorporation of a compound into cells or tissues.

The term "pharmaceutically acceptable derivative or prodrug" as used herein, refers to any pharmaceutically acceptable salt, ester, salt of an ester or other derivative of a compound of formula I, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the invention, or by separately reacting a purified compound in its free base form with a suitable organic or inorganic acid, and isolating the salt thus formed. Examples of pharmaceutically acceptable salts include those salts prepared by reaction of the compounds described herein with a mineral or organic acid or an inorganic base, such salts including, acetate, acrylate, adipate, alginate, aspartate, benzoate, benzenesulfonate, bisulfate, bisulfate, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds of the invention and their pharmaceutically acceptable acid addition salts. (See for example Berge et al., *J Pharm. Sci.* 1977, 66, 1-19.) Further, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, $N^+(C_{1-4}\ alkyl)_4$, and the like. Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they may contain. Water or oil-soluble or dispersible products may be obtained by such quaternization. See, for example, Berge et al., supra.

Pharmaceutically acceptable prodrugs of the compounds described herein include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Various forms of prodrugs are well known in the art. See for example Design of Prodrugs, Bundgaard, A. Ed., Elseview, 1985 and *Method in Enzymology*, Widder, K. et al., Ed.; Academic, 1985, vol. 42, p. 309-396; Bundgaard, H. "Design and Application of Prodrugs" in *A Textbook of Drug Design and Development*, Krosgaard-Larsen and H. Bundgaard, Ed., 1991, Chapter 5, p. 113-191; and Bundgaard, H., *Advanced Drug Delivery Review*, 1992, 8, 1-38, each of which is incorporated herein by reference. The prodrugs described herein include, but are not limited to, the following groups and combinations of these groups; amine derived prodrugs:

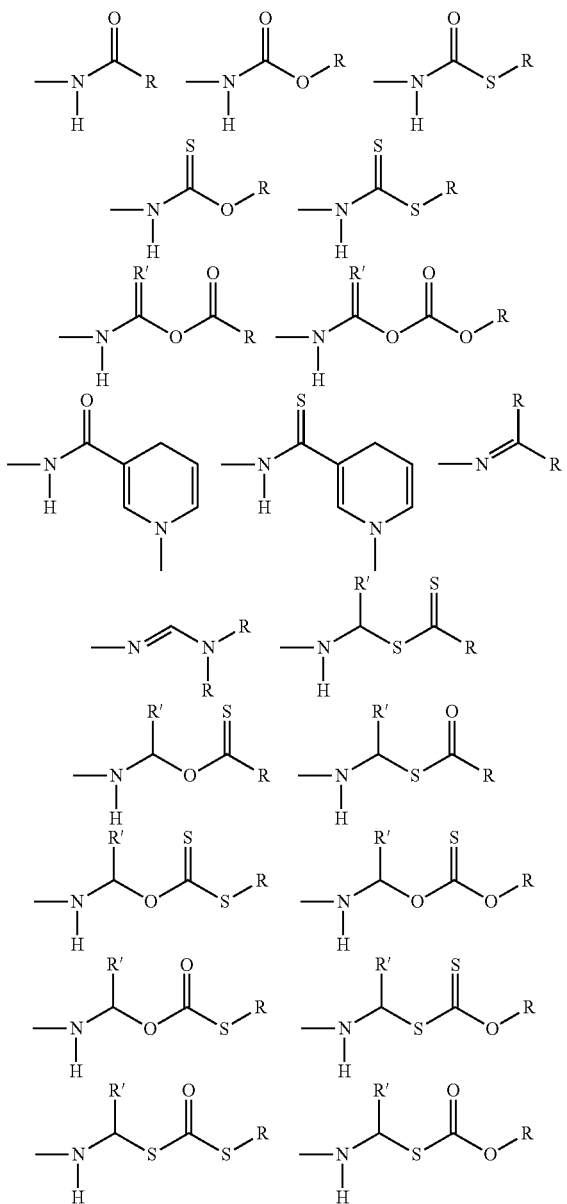

Hydroxy prodrugs include, but are not limited to acyloxyalkyl esters, alkoxycarbonyloxyalkyl esters, alkyl esters, aryl esters and disulfide containing esters.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "pharmaceutical combination", "administering an additional therapy", "administering an additional therapeutic agent" and the like, as used herein, refer to a pharmaceutical therapy resulting from the mixing or combining of more than one active ingredient and includes both fixed and non-fixed combinations of the active ingredients. The term "fixed combination" means that at least one of the compounds described herein, and at least one co-agent, are both administered to a patient simultaneously in the form of a single entity or dosage. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent(s) are administered in a single composition. In some embodiments, compounds of the invention and the other agent(s) are admixed in the composition.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics*, 9th Edition, McGraw-Hill (1996).

Compounds

Described herein are compounds of formula I:

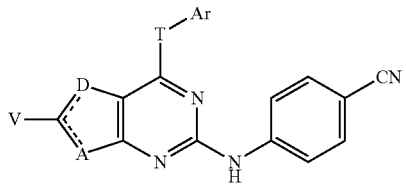

where the dashed line represents a double bond that may be located either between A and C(V) or between C(V) and D;

A is S or C(Z);

D is S or C(W);

provided that one and only one of A and D is S;

T is NH, O, or S;

W and Z are, independently, H, F, Cl, Br, $C_1$-$C_6$ alkyl; $C_2$-$C_6$ alkenyl; $OC_1$-$C_6$ alkyl; $C_3$-$C_6$ cycloalkyl; $OC_3$-$C_6$ cycloalkyl, phenyl, or benzyl, wherein alkyl, alkenyl, cycloalkyl, and phenyl groups and the phenyl moiety of the benzyl group are optionally substituted with 1-3 groups selected from halogen, $CF_3$, $C_1$-$C_3$ alkyl, and $OC_1$-$C_3$ alkyl V is H, halogen, $C_1$-$C_6$ alkyl;

or V and W, together with the ring atoms to which they are attached, form an additional, fused 5-, 6-, or 7-membered ring, optionally containing one or two heteroatoms, which additional ring may be saturated, unsaturated, or aromatic;

or V and Z, together with the ring atoms to which they are attached, form an additional, fused 5-, 6-, or 7-membered ring, optionally containing one or two heteroatoms, which additional ring may be saturated, unsaturated, or aromatic;

Ar is selected from (a), (b), (c), and (d) below:

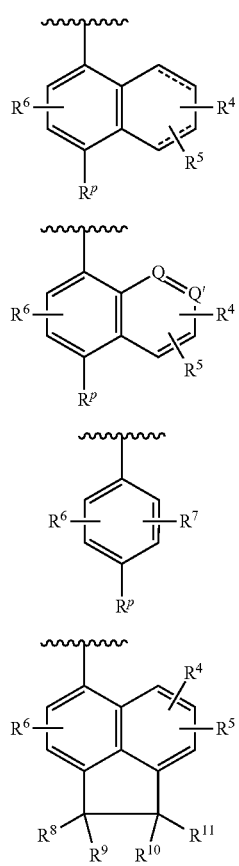

wherein each $R^P$ is selected from among methyl, ethyl, propyl, isopropyl, cyclopropylmethyl, or $C_3$-$C_6$ cycloalkyl, cyano, CH=CHCN, Cl, Br, I, acetyl, and $C_1$-$C_6$ alkyl-NH;

$R^4$, $R^5$ and each $R^6$ are independently selected from H, F, Cl, Br, $CH_3$, $CF_3$, $CH_2F$, $CHF_2$, isopropyl, cyclopropyl, $OCH_3$, OH, $OCF_3$, $NH_2$, and $NHCH_3$, or $R^6$ and $R^P$ on adjacent ring atoms, together with the ring atoms to which they are attached, form an additional fused five-membered ring;

Q and Q' are independently selected from N and CH;

$R^7$ is Cl, Br, I, $CH_3$, $CF_3$, $OCH_3$, isopropyl, cyclopropyl, t-butyl, or cyclobutyl; and $R^8$-$R^{11}$ are, independently, H or $CH_3$;

or a pharmaceutically acceptable salt, solvate, hydrate, polymorph, ester, tautomer or prodrug thereof.

In one generic embodiment this invention provides a compound of formula IA, in which the 6-linker T in formula I is T', which may be O or S.

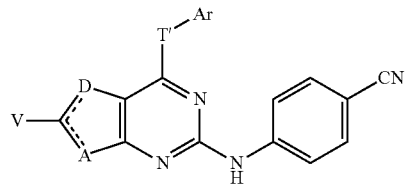

IA

In one subgeneric embodiment, the invention provides or contemplates a compound of formula IA where Ar is selected from 2-chloro-4-cyclopropyl phenyl; 2-methyl-4-cyclopropyl-naphth-1-yl; 2,6-dimethyl-4-cyanophenyl; 2,6-dimethoxy-4-cyanophenyl; 2,6-dimethyl-4-(2-cyanoethenyl) phenyl; 2,6-dimethoxy-4-(2-cyanoethenyl) phenyl; 2-methyl-4-cyclopropyl phenyl; 2,6-dimethyl-4-cyclopropyl phenyl; 2,6-di-trifluoromethyl-4-cyclopropyl phenyl; 2,4,6-trimethyl phenyl; and 2,6-dimethyl-4-acetyl phenyl.

In another subgeneric embodiment, the invention contemplates a compound of formula IA where Ar is selected from the following: 5-cyclopropyl-8-quinolyl; 5-isopropyl-8-quinolyl; 5-cyano-8-quinolyl; 5-cyclopropyl-7-trifluoromethyl-8-quinolyl; 5-acetyl-8-quinolyl; 5-cyano-7-methoxy-8-quinolyl; 5-cyano-7-methyl-8-quinolyl; 5-cyclopropyl-7-trifluoromethoxy-8-isoquinolyl; 5-cyano-8-isoquinolyl; 5-cyano-7-methoxy-8-isoquinolyl; 5-cyano-7-methyl-8-isoquinolyl; 5-cyclobutyl-7-difluoromethyl-8-isoquinolyl; 5,7-dimethyl-8-cinnolyl; 5-cyclopropyl-7-methyl-8-cinnolyl; and 5-(2-cyanoethenyl)-7-methyl-8-cinnolyl.

In another subgeneric embodiment, the invention provides a compound of formula IA-1

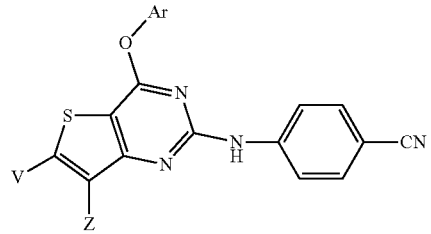

IA-1 where Ar, V, and Z are defined as for formula I.

In another subgeneric embodiment, the invention provides a compound of formula IA-2

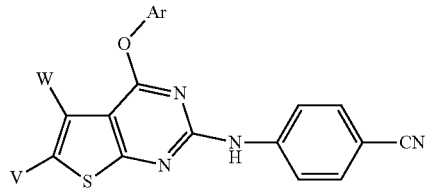

IA-2 where Ar, V, and W are defined as for formula I.

In another subgeneric embodiment, this invention provides a compound of formula IA-3

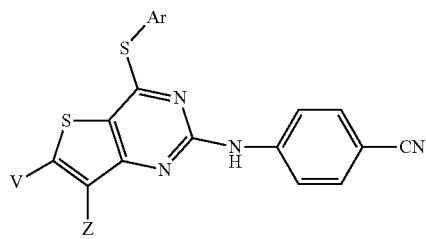

IA-3 where Ar, V and Z are defined as for formula I.

In another subgeneric embodiment, this invention provides a compound of formula IA-4

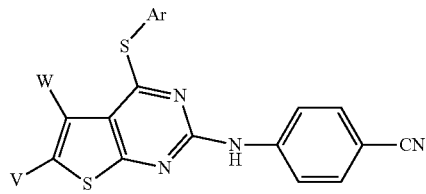

IA-4 where Ar, V and W are defined as for formula I.

In another generic embodiment, this invention provides a compound of formula IB

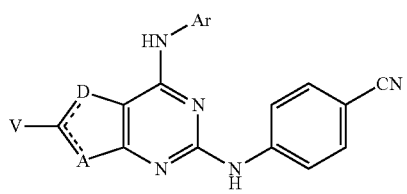

IB where all substituents are as described above.

In one subgeneric embodiment, the invention provides a compound of formula IB where Ar is (c).

In a more specific subgeneric embodiment, the invention provides a compound of formula IB where Ar is

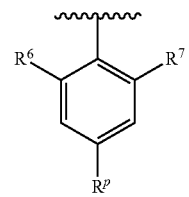

where RP is CN, CH=CHCN, or cyclopropyl; where $R^6$ and $R^7$ are either both methyl or both methoxy.

In another subgeneric embodiment, this invention provides a compound of formula IB-1.

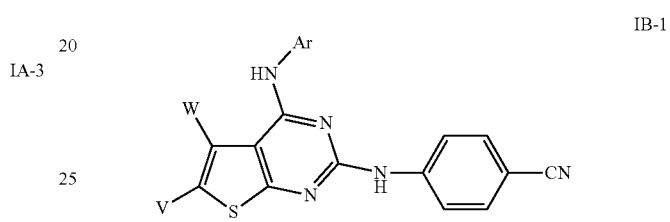

IB-1 where Ar, V and W are defined as for formula I.

In another subgeneric embodiment, this invention provides a compound of formula IB-2.

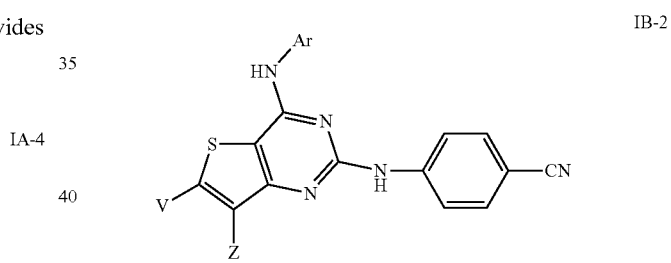

IB-2 where Ar, V and Z are as described above for formula I.

In more specific embodiments, the invention provides compounds of any of IA-1, IA-2, IA-3, IA-4, IB-1, IB-2, where Ar is (a).

In additional more specific embodiments, the invention provides compounds of any of IA-1, IA-2, IA-3, IA-4, IB-1, IB-2, where Ar is (b).

In additional more specific embodiments, the invention provides compounds of any of IA-1, IA-2, IA-3, IA-4, IB-1, IB-2, where Ar is (c).

In additional more specific embodiments, the invention provides compounds of any of IA-1, IA-2, IA-3, IA-4, IB-1, IB-2, where Ar is (d).

In another more specific subgeneric embodiment, this invention provides or contemplates a compound of formula IA-1, IA-2, IA-3, or IA-4, where Ar is 2,6-disubstituted-4-cyclopropyl, 2,6-disubstituted-4-acetyl, 2,4,6-trimethyl, 2,6-disubstituted-4-bromo, or 4-cyano-2,6-di-substituted phenyl.

In a still more specific subgeneric embodiment, this invention provides or contemplates compounds of formula IA-1, IA-2, IA-3, or IA-4, where Ar is 4-cyano-2,6-di-methoxy phenyl or 4-cyano-2,6-di-methyl phenyl.

In another still more specific subgeneric embodiment, this invention provides or contemplates compounds of formula IA-1, IA-2, IA-3, or IA-4, where V is H, halo, or methyl.

In another still more specific subgeneric embodiment, this invention provides or contemplates compounds of formula IA-1, IA-2, IA-3, or IA-4, where A is S and W is H, phenyl, or benzyl.

In another still more specific subgeneric embodiment, this invention provides or contemplates a compound of formula IA-1, IA-2, IA-3, or IA-4, where A is S and W is H, $C_3$-$C_6$ cycloalkyl, or $OC_3$-$C_6$ cycloalkyl.

In another still more specific subgeneric embodiment, this invention provides or contemplates compounds of formula IA-1, IA-2, IA-3, or IA-4, where A is S and W is H, unsubstituted $C_1$-$C_4$ alkyl, monosubstituted $C_1$-$C_4$ alkyl, or $C_2$-$C_3$ alkenyl.

In another still more specific subgeneric embodiment, this invention provides or contemplates compounds of formula IA-1, IA-2, IA-3, or IA-4, where A is S and W is H, halo, halomethyl, or methyl.

In another still more specific subgeneric embodiment, this invention provides or contemplates compounds of formula IA-1, IA-2, IA-3, or IA-4, where A is S and V and W, together with the ring atoms to which they are attached, form an additional, fused 5-, 6-, or 7-membered carbocyclic ring.

In another still more specific subgeneric embodiment, this invention provides or contemplates compounds of formula IA-1, IA-2, IA-3, or IA-4, where A is S and V and W, together with the ring atoms to which they are attached, form an additional, fused 5-, 6-, or 7-membered ring, which ring contains one or two heteroatoms selected from O, N, and S.

In another still more specific subgeneric embodiment, this invention provides or contemplates compounds of formula IA-1, IA-2, IA-3, or IA-4, where D is S and Z is H, $C_1$-$C_6$ alkyl, or $C_2$-$C_6$ alkenyl.

In another still more specific subgeneric embodiment, this invention provides or contemplates compounds of formula IA-1, IA-2, IA-3, or IA-4, where D is S and Z is H, $C_3$-$C_6$ cycloalkyl, or $OC_3$-$C_6$ cycloalkyl.

In another still more specific subgeneric embodiment, this invention provides or contemplates compounds of formula IA-1, IA-2, IA-3, or IA-4, where D is S and Z is H, unsubstituted $C_1$-$C_4$ alkyl, monosubstituted $C_1$-$C_4$ alkyl, or $C_2$-$C_3$ alkenyl.

In another still more specific subgeneric embodiment, this invention provides or contemplates compounds of formula IA-1, IA-2, IA-3, or IA-4, where D is S and Z is H, halo, halomethyl, or methyl.

In another still more specific subgeneric embodiment, this invention provides or contemplates a compound of formula IA-1, IA-2, IA-3, or IA-4, where D is S and Z is H, phenyl, or benzyl.

In another still more specific subgeneric embodiment, this invention provides or contemplates compounds of formula IA-1, IA-2, IA-3, or IA-4, where D is S and V and Z, together with the ring atoms to which they are attached, form an additional, fused 5-, 6-, or 7-membered carbocyclic ring.

In another still more specific subgeneric embodiment, this invention provides or contemplates compounds of formula IA-1, IA-2, IA-3, or IA-4, where D is S and V and Z, together with the ring atoms to which they are attached, form an additional, fused 5-, 6-, or 7-membered ring, which ring contains one or two heteroatoms selected from O, N, and S.

Synthetic Procedures

In another aspect, methods for synthesizing the compounds described herein are provided. In some embodiments, the compounds described herein can be prepared by the methods described below. The procedures and examples below are intended to illustrate those methods. Neither the procedures nor the examples should be construed as limiting the invention in any way. Compounds described herein may also be synthesized using standard synthetic techniques known to those of skill in the art or using methods known in the art in combination with methods described herein. In additions, solvents, temperatures and other reaction conditions presented herein may vary according to the practice and knowledge of those of skill in the art.

The starting materials used for the synthesis of the compounds as described herein can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and WITS, PROTECTIVE GROUPS IN ORGANIC SYNTHESIS 3$^{rd}$ Ed., (Wiley 1999) (all of which are incorporated by reference in their entirety). General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein. As a guide the following synthetic methods may be utilized.

Formation of Covalent Linkages by Reaction of an Electrophile with a Nucleophile The compounds described herein can be modified using various electrophiles or nucleophiles to form new functional groups or substituents. The table below entitled "Examples of Covalent Linkages and Precursors Thereof" lists selected examples of covalent linkages and precursor functional groups which yield and can be used as guidance toward the variety of electrophiles and nucleophiles combinations available. Precursor functional groups are shown as electrophilic groups and nucleophilic groups.

| Examples of Covalent Linkages and Precursors Thereof | | |
|---|---|---|
| Covalent Linkage Product | Electrophile | Nucleophile |
| Carboxamides | Activated esters | Amines/anilines |
| Carboxamides | Acyl azides | Amines/anilines |
| Carboxamides | Acyl halides | Amines/anilines |
| Esters | Acyl halides | Alcohols/phenols |
| Esters | Acyl nitriles | Alcohols/phenols |
| Carboxamides | Acyl nitriles | Amines/anilines |
| Imines | Aldehydes | Amines/anilines |
| Hydrazones | Aldehydes or ketones | Hydrazines |
| Oximes | Aldehydes or ketones | Hydroxylamines |
| Alkyl amines | Alkyl halides | Amines/anilines |
| Esters | Alkyl halides | Carboxylic acids |
| Thioethers | Alkyl halides | Thiols |
| Ethers | Alkyl halides | Alcohols/phenols |
| Thioethers | Alkyl sulfonates | Thiols |
| Esters | Alkyl sulfonates | Carboxylic acids |
| Ethers | Alkyl sulfonates | Alcohols/phenols |
| Esters | Anhydrides | Alcohols/phenols |
| Carboxamides | Anhydrides | Amines/anilines |
| Thiophenols | Aryl halides | Thiols |
| Aryl amines | Aryl halides | Amines |
| Thioethers | Azindines | Thiols |
| Boronate esters | Boronates | Glycols |
| Carboxamides | Carboxylic acids | Amines/anilines |
| Esters | Carboxylic acids | Alcohols |
| Hydrazines | Hydrazides | Carboxylic acids |
| N-acylureas or Anhydrides | Carbodiimides | Carboxylic acids |

-continued

Examples of Covalent Linkages and Precursors Thereof

| Covalent Linkage Product | Electrophile | Nucleophile |
|---|---|---|
| Esters | Diazoalkanes | Carboxylic acids |
| Thioethers | Epoxides | Thiols |
| Thioethers | Haloacetamides | Thiols |
| Ammotriazines | Halotriazines | Amines/anilines |
| Triazinyl ethers | Halotriazines | Alcohols/phenols |
| Amidines | Imido esters | Amines/anilines |
| Ureas | Isocyanates | Amines/anilines |
| Urethanes | Isocyanates | Alcohols/phenols |
| Thioureas | Isothiocyanates | Amines/anilines |
| Thioethers | Maleimides | Thiols |
| Phosphite esters | Phosphoramidites | Alcohols |
| Silyl ethers | Silyl halides | Alcohols |
| Alkyl amines | Sulfonate esters | Amines/anilines |
| Thioethers | Sulfonate esters | Thiols |
| Esters | Sulfonate esters | Carboxylic acids |
| Ethers | Sulfonate esters | Alcohols |
| Sulfonamides | Sulfonyl halides | Amines/anilines |
| Sulfonate esters | Sulfonyl halides | Phenols/alcohols |

Use of Protecting Groups

In the reactions described, it may be necessary to protect reactive functional groups, for example hydroxy, amino, imino, thio or carboxy groups, where these are desired in the final product, to avoid their unwanted participation in the reactions. Protecting groups are used to block some or all reactive moieties and prevent such groups from participating in chemical reactions until the protective group is removed. It is preferred that each protective group be removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a Pd-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Protecting or blocking groups may be selected from:

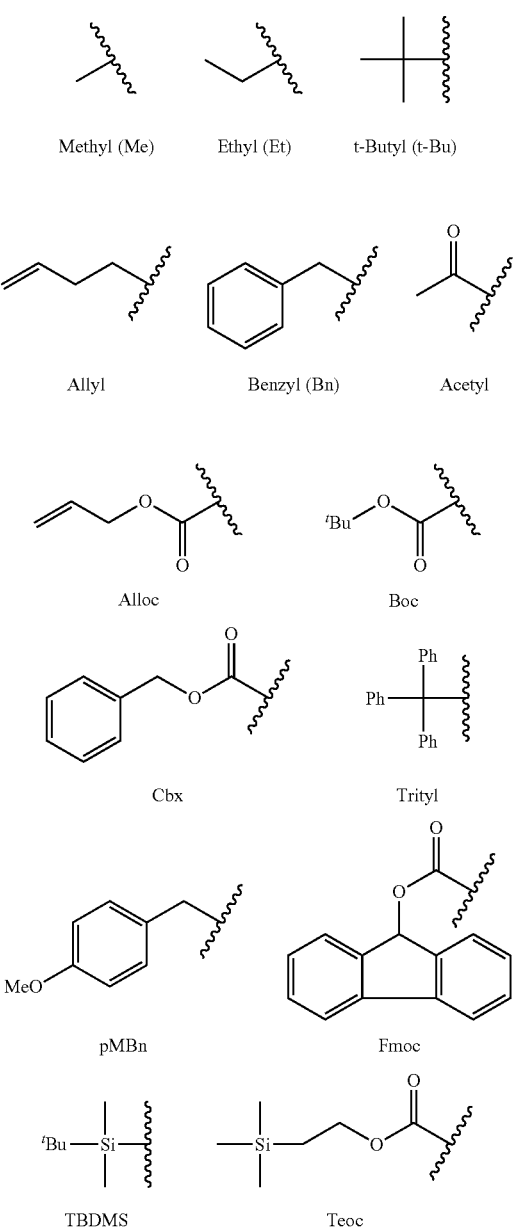

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference in their entirety.

Preparing Compounds of formula I

Compounds of this invention are prepared according to the synthetic routes presented in schemes 1-3 and following typical synthetic procedures. Where appropriate, standard blocking or protecting methods well-known in the art of synthetic organic chemistry may be required. Such circumstances will be readily recognized by persons of skill in the art.

Scheme 1

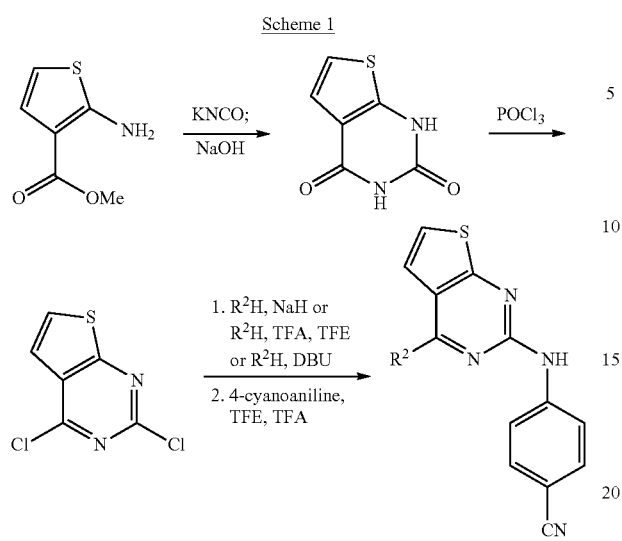

R2H is aniline, phenol or thiophenol, optionally substituted

Scheme 2

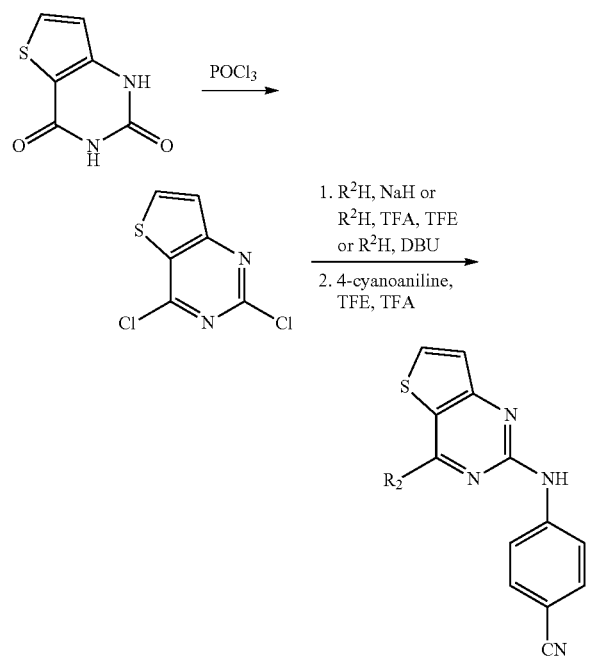

Scheme 3

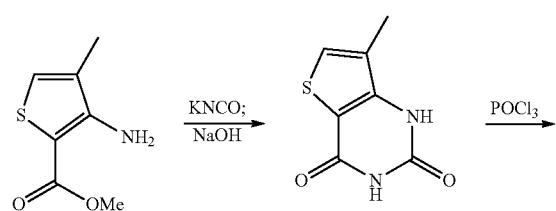

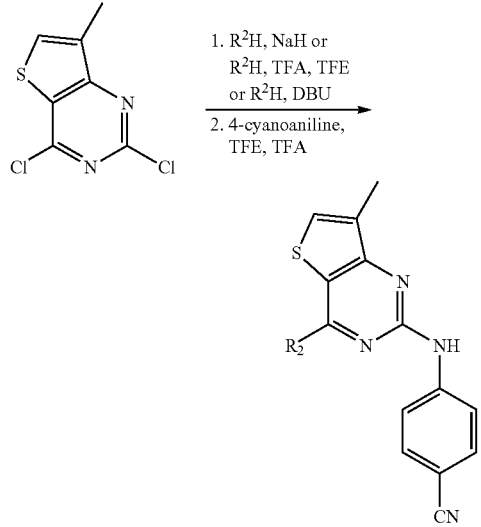

Further Forms of Compounds of formula I

Isomers of Compounds of Formula I

The compounds described herein may exist as geometric isomers. The compounds described herein may possess one or more double bonds. The compounds presented herein include all cis, trans, syn, anti, entgegen (E), and zusammen (Z) isomers as well as the corresponding mixtures thereof. In some situations, compounds may exist as tautomers. The compounds described herein include all possible tautomers within the formulas described herein. The compounds described herein may possess one or more chiral centers and each center may exist in the R or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion may also be useful for the applications described herein. The compounds described herein can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds described herein, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chiral chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981, herein incorporated by reference in its entirety.

Labeled Compounds of Formula I

Also described herein are isotopically-labeled compounds of formula I and methods of treating disorders. For example, the invention provides for methods of treating diseases, by administering isotopically-labeled compounds of formula I. The isotopically-labeled compounds of formula I can be administered as pharmaceutical compositions. Thus, compounds of formula I also include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chloride, such as $^2$H, $^3$H, $^{13}$C, $^{14}$C, $^{15}$N, $^{18}$O, $^{17}$O, $^{31}$P, $^{35}$S, $^{18}$F, and $^{36}$Cl, respectively. Compounds described herein, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds of formula I, for example those into which radioactive isotopes such as $^3$H and $^{14}$C are incorporated, are useful in drug and/or substrate tissue distribution assays. Tritiated, i. e., $^3$H and carbon-14, i. e., $^{14}$C, isotopes are particularly preferred for their ease of preparation and detectability. Further, substitution with heavier isotopes such as deuterium, i. e., $^2$H, can afford certain therapeutic advantages resulting from greater metabolic stability, for example increased in vivo half-life or reduced dosage requirements and, hence, may be preferred in some circumstances. Isotopically labeled compounds, pharmaceutically acceptable salt, ester, prodrug, solvate, hydrate or derivative thereof can generally be prepared by carrying out procedures described herein, by substituting a readily available isotopically labeled reagent for a non-isotopically labeled reagent.

The compounds described herein may be labeled by other means, including, but not limited to, the use of chromophores or fluorescent moieties, bioluminescent labels, or chemiluminescent labels.

Pharmaceutically Acceptable Salts of Compounds of Formula I

Also described herein are pharmaceutically acceptable salts of compounds of formula I and methods of treating disorders. For example, the invention provides for methods of treating diseases, by administering pharmaceutically acceptable salts of compounds of formula I. The pharmaceutically acceptable salts of compounds of formula I can be administered as pharmaceutical compositions.

Thus, the compounds described herein can be prepared as pharmaceutically acceptable salts formed when an acidic proton present in the parent compound either is replaced by a metal ion, for example an alkali metal ion, an alkaline earth ion, or an aluminum ion; or coordinates with an organic base. Base addition salts can also be prepared by reacting the free acid form of the compounds described herein with a pharmaceutically acceptable inorganic or organic base, including, but not limited to organic bases such as ethanolamine, diethanolamine, triethanolamine, tromethamine, N-methylglucamine, and the like and inorganic bases such as aluminum hydroxide, calcium hydroxide, potassium hydroxide, sodium carbonate, sodium hydroxide, and the like. In addition, the salt forms of the disclosed compounds can be prepared using salts of the starting materials or intermediates.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, Q-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

Solvates of Compounds of Formula I

Also described herein are solvates of compounds of formula I and methods of treating disorders. For example, the invention provides for methods of treating diseases, by administering solvates of compounds of formula I. The solvates of compounds of formula I can be administered as pharmaceutical compositions.

Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Polymorphs of Compounds of Formula I

Also described herein are polymorphs of compounds of formula I and methods of treating disorders. For example, the invention provides for methods of treating diseases, by administering polymorphs of compounds of formula I. The polymorphs of compounds of formula I can be administered as pharmaceutical compositions.

Thus, the compounds described herein include all their crystalline forms, known as polymorphs. Polymorphs include the different crystal packing arrangements of the same elemental composition of a compound. Polymorphs may have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Prodrugs of Compounds of Formula I

Also described herein are prodrugs of compounds of formula I and methods of treating disorders. For example, the invention provides for methods of treating diseases, by administering prodrugs of compounds of formula I. The prodrugs of compounds of formula I can be administered as pharmaceutical compositions.

Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound as described herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyamino acid) bonded to an acid group where the peptide is metabolized to reveal the active moiety.

Prodrugs may be designed as reversible drug derivatives, for use as modifiers to enhance drug transport to site-specific tissues. The design of prodrugs to date has been to increase the effective water solubility of the therapeutic compound for targeting to regions where water is the principal solvent. See, e.g., Fedorak et al., *Am. J. Physiol.,* 269:G210-218 (1995); McLoed et al., *Gastroenterol,* 106:405-413 (1994); Hochhaus et al., *Biomed. Chrom.,* 6:283-286 (1992); J. Larsen and H. Bundgaard, *Int. J. Pharmaceutics,* 37, 87 (1987); J. Larsen et al., *Int. J Pharmaceutics,* 47, 103 (1988); Sinkula et al., *J Pharm. Sci.,* 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design,* American Pharmaceutical Association and Pergamon Press, 1987, all incorporated herein in their entirety.

Additionally, prodrug derivatives of compounds described herein can be prepared by methods known to those of ordinary skill in the art (e.g., for further details see Saulnier et al., (1994), Bioorganic and Medicinal Chemistry Letters, Vol. 4, p. 1985). By way of example only, appropriate prodrugs can be prepared by reacting a non-derivatized compound of formula I with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds may be a prodrug for another derivative or active compound.

In some embodiments, prodrugs include compounds wherein an amino acid residue, or a polypeptide chain of two or more (e. g., two, three or four) amino acid residues is covalently joined through an amide or ester bond to a free amino, hydroxy or carboxylic acid group of compounds of the present invention. The amino acid residues include but are not limited to the 20 naturally occurring amino acids commonly designated by three letter symbols and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. Additional types of prodrugs are also encompassed.

Compounds of formula I having free amino, amido, hydroxy or carboxylic groups can be converted into prodrugs. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews* 1996, 19, 115. Carbamate prodrugs of hydroxy and amino groups are also included, as are carbonate prodrugs, sulfonate esters and sulfate esters of hydroxy groups.

Derivatization of hydroxy groups as (acyloxy) methyl and (acyloxy) ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Sites on the aromatic ring portions of compounds of formula I may be susceptible to various metabolic reactions, therefore incorporation of appropriate substituents on the aromatic ring structures, can reduce, minimize or eliminate this metabolic pathway.

Methods

The present invention also provides methods for treating or ameliorating HW disease and related diseases. The method includes administering a therapeutically effective dosage of at least one compound of the invention to a subject suffering from HIV disease or HIV-related diseases. The invention also provides a method of combination therapy in which one or more compound of the invention is administered in combination with one or more other compound having activity against HW disease or HIV-related disease.

Furthermore, the invention provides methods for inhibiting drug resistant HW mutants. The high replication rate of HIV leads to genetic variants (mutants), especially when selective pressure is introduced in the form of drug treatment. The mutants frequently display resistance to anti-viral agents previously administered to the patient. Switching agents or using combination therapies may decrease or delay resistance, but because viral replication is not completely suppressed in single drug treatment or even with a two-drug combination, drug-resistant viral strains ultimately emerge. Triple drug combinations employing one (or two) nucleoside analogs and two (or one) non-nucleoside inhibitor (NNI) targeting RT provide a very promising therapy to overcome the drug resistance problem. RT mutant strains resistant to such a triple action drug combination would most likely not be able to function. Many mutant strains have been characterized as resistant to NNI compounds, including L1001, K103N, V106A, E 138K, Y181C and Y188H. In particular, the Y181C and K103N mutants may be the most difficult to treat, because they are resistant to most of the NNI compounds that have been examined.

Pharmaceutical Compositions

Described herein are pharmaceutical compositions. In some embodiments, the pharmaceutical compositions comprise an effective amount of a compound formula I, or a pharmaceutically acceptable salt, ester, prodrug, solvate, hydrate or derivative thereof. In some embodiments, the pharmaceutical compositions comprise an effective amount of a compound formula I, or a pharmaceutically acceptable salt, ester, prodrug, solvate, hydrate or derivative thereof and at least one pharmaceutically acceptable carrier. In some embodiments the pharmaceutical compositions are for the treatment of disorders. In some embodiments the pharmaceutical compositions are for the treatment of disorders in a mammal. In some embodiments the pharmaceutical compositions are for the treatment of disorders in a human. In some embodiments the pharmaceutical compositions are for the treatment of HIV/AIDS.

Modes of Administration

Described herein are compounds of formula I or a pharmaceutically acceptable salt, solvate, polymorph, ester, tautomer or prodrug thereof. Also described, are pharmaceutical compositions comprising a compound of formula I or a pharmaceutically acceptable salt, solvate, polymorph, ester, tautomer or prodrug thereof. The compounds and compositions described herein may be administered either alone or in combination with pharmaceutically acceptable carriers, excipients or diluents, in a pharmaceutical composition, according to standard pharmaceutical practice.

Administration of the compounds and compositions described herein can be effected by any method that enables delivery of the compounds to the site of action. These methods include oral routes, intraduodenal routes, parenteral injection (including intravenous, subcutaneous, intraperitoneal, intramuscular, intravascular or infusion), topical, and rectal administration. For example, compounds described herein can be administered locally to the area in need of treatment. This may be achieved by, for example, but not limited to, local infusion during surgery, topical application, e.g., cream, ointment, injection, catheter, or implant, said implant made, e.g., out of a porous, non-porous, or gelatinous material, including membranes, such as sialastic membranes, or fibers. The administration can also be by direct injection at the site (or former site) of a tumor or neoplastic or pre-neoplastic tissue. Those of ordinary skill in the art are familiar with formulation and administration techniques that can be employed with the compounds and methods of the invention, e.g., as discussed in Goodman and Gilman, The Pharmacological Basis of Therapeutics, current ed.; Pergamon; and Remington's, Pharmaceutical *Sciences* (current edition), Mack Publishing Co., Easton, Pa.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the subject invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

Pharmaceutical preparations may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical preparations may also be formulated in rectal compositions such as suppositories or retention enemas, e.g., containing conventional suppository bases such as cocoa butter, polyethylene glycol, or other glycerides.

Pharmaceutical preparations may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical preparations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Pharmaceutical preparations for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Formulations

The compounds or compositions described herein can be delivered in a vesicle, e.g., a liposome (see, for example, Langer, *Science* 1990, 249,1527-1533; Treat et al., *Liposomes in the Therapy of Infectious Disease and Cancer*, Lopez-Bernstein and Fidler, Ed., Liss, N.Y., pp. 353-365, 1989).The compounds and pharmaceutical compositions described herein can also be delivered in a controlled release system. In one embodiment, a pump may be used (see, Sefton, 1987, CRC Crit. Ref. Biomed. Eng. 14:201; Buchwald et al. *Surgery,* 1980 88, 507; Saudek et al. *N Engl. J. Med.* 1989, 321, (574). Additionally, a controlled release system can be placed in proximity of the therapeutic target. (See, Goodson, Medical Applications of Controlled Release, 1984, Vol. 2, pp. 115-138). The pharmaceutical compositions described herein can also contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions, and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be un-coated or coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, or cellulose acetate butyrate may be employed as appropriate. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

Pharmaceutical compositions may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening agents, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

Pharmaceutical compositions may be in the form of a sterile injectable aqueous solution. Among the acceptable vehicles and solvents that may be employed are water, Ringer's solution and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion. The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump. The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Pharmaceutical compositions may also be administered in the form of suppositories for rectal administration of the drug. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing a compound or composition of the invention can be used. As used herein, topical application can include mouth washes and gargles.

Pharmaceutical compositions may be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

Doses

The amount of pharmaceutical compositions administered will firstly be dependent on the mammal being treated. In the instances where pharmaceutical compositions are administered to a human subject, the daily dosage will normally be determined by the prescribing physician with the dosage generally varying according to the age, sex, diet, weight, general health and response of the individual patient, the severity of the patient's symptoms, the precise indication or condition being treated, the severity of the indication or condition being treated, time of administration, route of administration, the disposition of the composition, rate of excretion, drug combination, and the discretion of the prescribing physician. Also, the route of administration may vary depending on the condition and its severity. Preferably, the pharmaceutical composition is in unit dosage form. In such form, the preparation is subdivided into unit doses containing appropriate quantities of the active component, e.g., an effective amount to achieve the desired purpose. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. The amount and frequency of administration of the compounds described herein, and if applicable other therapeutic agents and/or therapies, will be regulated according to the judgment of the attending clinician (physician) considering such factors as described above. Thus the amount of pharmaceutical composition to be administered may vary widely. Administration may occur in an amount of between about 0.001 mg/kg of body weight to about 100 mg/kg of body weight per day (administered in single or divided doses), more preferably at least about 0.1 mg/kg of body weight per day. A particular therapeutic dosage can include, e.g., from about 0.01 mg to about 7000 mg of compound, and preferably includes, e.g., from about 0.05 mg to about 2500 mg. The quantity of active compound in a unit dose of preparation may be varied or adjusted from about 0.1 mg to 1000 mg, preferably from about 1 mg to 300 mg, more preferably 10 mg to 200 mg, according to the particular application. In some instances, dosage levels below the lower limit of the aforesaid range may be more than adequate, while in other cases still larger doses may be employed without causing any harmful side effect, e.g. by dividing such larger doses into several small doses for administration throughout the day. The amount administered will vary depending on the particular $IC_{50}$ value of the compound used. In combinational applications in which the compound is not the sole therapy, it may be possible to administer lesser amounts of compound and still have therapeutic or prophylactic effect.

Dosage Forms

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 18th Edition (1990).

Combination Therapies

The compounds described herein or a pharmaceutically acceptable salt, solvate, polymorph, ester, tautomer or prodrug thereof may be administered as a sole therapy. The compounds described herein or a pharmaceutically acceptable salt, solvate, polymorph, ester, tautomer or prodrug thereof may also be administered in combination with another therapy or therapies.

By way of example only, if one of the side effects experienced by a patient upon receiving one of the compounds described herein is hypertension, then it may be appropriate to administer an anti-hypertensive agent in combination with the compound. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. By way of example only, in a treatment for HIV/AIDS involving administration of one of the compounds described herein, increased therapeutic benefit may result by also providing the patient with another therapeutic agent for HIV/AIDS. In any case, regardless of the disease, disorder or condition being treated, the overall benefit experienced by the patient may simply be additive of the two therapeutic agents or the patient may experience a synergistic benefit.

Other therapies include, but are not limited to administration of other therapeutic agents. In the instances where the compounds described herein are administered with other therapeutic agents, the compounds described herein need not be administered in the same pharmaceutical composition as other therapeutic agents, and may, because of different physical and chemical characteristics, be administered by a different route. For example, the compounds/compositions may be administered orally to generate and maintain sufficient blood levels thereof, while the other therapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician. The particular choice of compound will depend upon the diagnosis of the attending physicians and their judgment of the condition of the patient and the appropriate treatment protocol.

The present invention provides methods for treating or ameliorating HIV disease and related diseases. The method includes administering a therapeutically effective dosage of at least one compound of the invention to a subject suffering from HIV disease or HIV-related diseases. The invention also provides a method of combination therapy in which one or more compound of the invention is administered in combination with one or more other compound having activity against HIV disease or HIV-related disease.

Kits

The compounds, compositions and methods described herein provide kits for the treatment of disorders, such as the ones described herein. These kits comprise a compound, compounds or compositions described herein in a container and, optionally, instructions teaching the use of the kit according to the various methods and approaches described herein. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

The compounds described herein can be utilized for diagnostics and as research reagents. For example, the compounds described herein, either alone or in combination with other compounds, can be used as tools in differential and/or combinatorial analyses to elucidate expression patterns of genes expressed within cells and tissues. As one non-limiting example, expression patterns within cells or tissues treated with one or more compounds are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Besides being useful for human treatment, the compounds and formulations of the present invention are also useful for veterinary treatment of companion animals, exotic animals and farm animals, including mammals, rodents, and the like. More preferred animals include horses, dogs, and cats.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

I. Chemical Syntheses

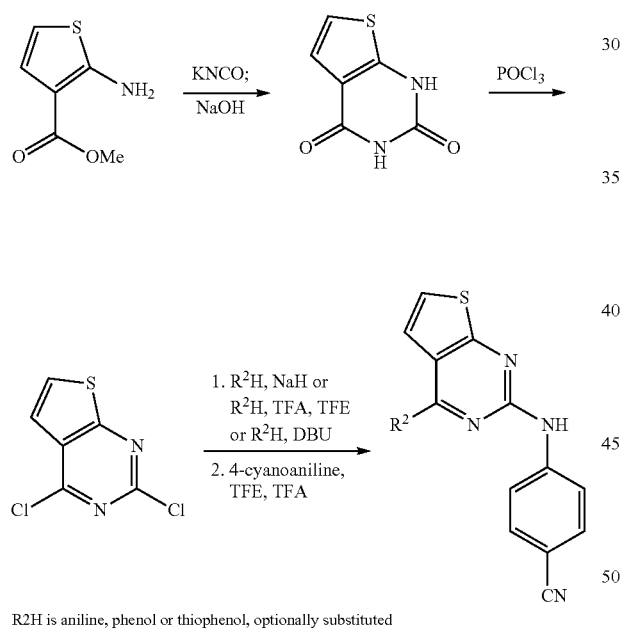

R2H is aniline, phenol or thiophenol, optionally substituted

Commercially available methyl-2-aminothiophene-3-carboxylate was cyclized to thieno[2,3]pyrimidine by first treating with potassium cyanate followed by refluxing in 6% aqueous sodium hydroxide solution. Chlorination with phosphonyl chloride provided the dichloro thienopyrimidine. $R^2H$ (defined as a substituted or unsubstituted aniline, a substituted or unsubstituted phenol or a substituted or unsubstituted thiophenol) was coupled on the ring system with trifluoroethanol and trifluoroacetic acid (when $R^2H$ is a substituted or unsubstituted aniline), sodium hydride (when $R^2H$ is a substituted or unsubstituted phenol), or DBU (when $R^2H$ is a substituted or unsubstituted thiophenol). 4-Amino benzonitrile was coupled in the presence of trifluoroethanol and trifluoroacetic acid to provide a series of thieno[2,3-d] pyrimidine compounds with various $R^2$ substitutions.

Example 1

Thieno[2,3-d]pyrimidine-2,4(1H,3H)-dione

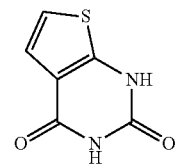

To a stirred solution of methyl-2-aminothiophene-3-carboxylate (2.03 g, 12.9 mmol) in acetic acid (65 mL) and water (6.5 mL) was added a solution of potassium cyanate (3.14 g, 38.7 mmol) dissolved in water (10.4 mL) dropwise via syringe. The reaction was stirred at room temperature for 15 h, upon completion of the reaction; the reaction mixture was concentrated to 75% and filtered off white solid. To the solid was added 6% aqueous sodium hydroxide (16 mL) and refluxed for 2 h. After cooling to room temperature, the solution was acidified using 12N HCl to pH=6. The resultant precipitate was filtered, washed with water and dried in a vacuum oven overnight to give 546 mg (25%) of the title compound as an orange solid which was used without any further purification:

$^1$H NMR (DMSO, 300 MHz) δ 7.06 (d, J=5.7 Hz, 1H), 7.1 (d, J=5.7 Hz, 1H), 11.1 (broad s, 1H), 11.9 (broad s, 1H).

Example 2

2,4-Dichlorothieno[2,3-d]pyrimidine

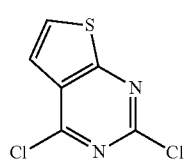

A mixture of thieno[2,3-d]pyrimidine-2,4(1H,3H)-dione (100 mg, 0.59 mmol) and phosphonyl chloride (2 mL, 21.5 mmol) was heated at 116° C. for 3 h. Upon completion of the reaction, the reaction mixture was poured into ice and extract with ethyl acetate 3 times. The combined organic layers were washed with brine, dried over $Na_2SO_4$, filtered and concentrated in vacuo. Purification by column chromatography, eluting with Hexanes/Ethyl Acetate (9:1) afforded the product as a white solid (48.1 mg, 40%):

$^1$H NMR (DMSO, 300 MHz) δ 7.6 (d, J=6.3 Hz, 1H), 8.13(d, J=5.7 Hz, 1H).

Example 3

2-Chloro-4-(mesityloxy)thieno[2,3-d]pyrimidine

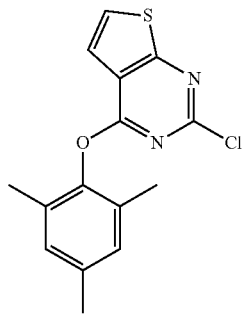

A stirred suspension of NaH (9.5 mg, 0.24 mmol) in dry THF (1 mL) was added 2,4,6-trimethyl phenol (32.1 mg, 0.24 mmol) and stirred at room temperature for 30 min under Argon. The reaction mixture was added to a solution of 2,4-dichlorothieno[2,3-d]pyrimidine (48.1 mg, 0.24 mmol) in dry THF (1.5 mL) at 0° C. and allow it to slowly warmed up to room temperature. After stirring the reaction for 4 h, the resulting mixture was diluted with water and washed with EtOAc. The combined organic layers were washed with water, brine, dried over Na$_2$SO$_4$, filtered and concentrated in vacuo. The crude product was purified by column chromatography, eluting with hexanes/ethyl acetate (9:1) to give the product as a white solid (71 mg, 97%):

$^1$H NMR (DMSO, 300 MHz) δ 2.0 (s, 6H), 2.27 (s, 3H), 6.98 (s, 2H), 7.65 (d, J=6.0 Hz, 1H), 7.75 (d, J=5.7 Hz, 1H).

Example 4

4-(4-Mesityloxy)thieno[2,3-d]pyrimidin-2-ylamino) benzonitrile

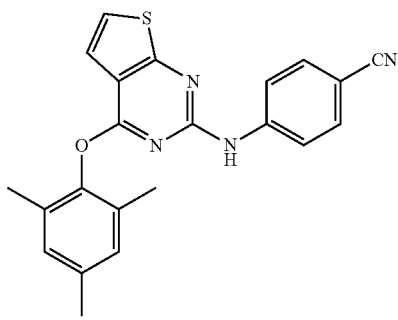

To a solution of 2-chloro-4-(mesityloxy)thieno[2,3-d]pyrimidine (71 mg, 0.23 mmol), TFA (0.15 mL, 1.84 mmol) in TFE (1.3 mL) was added 4-aminobenzonitrile (110 mg, 0.93 mmol) in a sealed tube. The reaction was stirred at 90° C. for 15 h. Reaction mixture was diluted with ethyl acetate (5 mL) and washed with saturated NaHCO$_3$ (3×10 mL). The combined organic layers were washed with brine, dried over Na$_2$SO$_4$, filtered and concentrated in vacuo. The crude product was purified by prep plate eluting with Hexanes/ethyl acetate (3:1) give product as white solid (29 mg, 33%):

$^1$H NMR (DMSO, 300 MHz) δ 2.0 (s, 6H), 2.31 (s, 3H), 7.02 (s, 2H), 7.46 (d, J=8.1 Hz, 2H), 7.51 (d, J=6.3 Hz, 1H), 7.55 (d, J=5.4 Hz, 1H), 7.62 (d, J=9.0 Hz, 2H), 10.15 (s, 1H).

Example 5

4-(2-Chlorothieno[2,3-d]pyrimidin-4-yloxy)-3,5-dimethylbenzonitrile

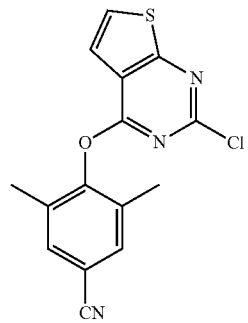

A stirred suspension of NaH (85 mg, 2.12 mmol) in dry THF (12 mL) was added 4-hydroxy-3,5-dimethyl benzonitrile (311 mg, 2.12 mmol) and stirred at room temperature for 30 min under Argon. The reaction mixture was added to a solution of 2,4-dichlorothieno[2,3-d]pyrimidine (434 mg, 2.12 mmol) in dry THF (10 mL) and heated at 50° C. for 2 h, the resulting mixture was diluted with water and washed with EtOAc. The combined organic layers were washed with water, brine, dried over Na$_2$SO$_4$, filtered and concentrated in vacuo. The crude product was purified by column chromatography, eluting with hexanes/ethyl acetate (5:1) to give the product as a white solid (188 mg, 28%):

$^1$H NMR (DMSO, 300 MHz) δ 2.10 (s, 6H), 7.72 (d, J=5.7 Hz, 1H), 7.75 (s, 2H), 8.02 (d, J=6.0 Hz, 1H).

Example 6

4-(2-(4-Cyanophenylamino)thieno[2,3-d]pyrimidin-4-yloxy)-3,5-dimethylbenzonitrile

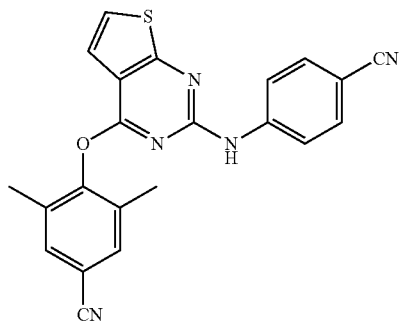

To a solution of 4-(2-chlorothieno[2,3-d]pyrimidin-4-yloxy)-3,5-dimethylbenzonitrile (188 mg, 0.59 mmol), TFA (0.37 mL, 4.75 mmol) in TFE (2.5 mL) was added 4-aminobenzonitrile (280 mg, 2.37 mmol) in a sealed tube. The reaction was stirred at 90° C. for 2 d. Reaction mixture was diluted with ethyl acetate (5 mL) and washed with saturated NaHCO₃ (3×10 mL). The combined organic layers were washed with brine, dried over Na₂SO₄, filtered and concentrated in vacuo. The crude product was purified by HPLC afforded the product as white solid (34 mg, 14%):

¹H NMR (DMSO, 300 MHz) δ 2.12 (s, 6H), 7.60-7.50 (m, 6H), 10.12 (s, 1H).

Example 7

2-Chloro-N-mesitylthieno[2,3-d]pyrimidin-4-amine

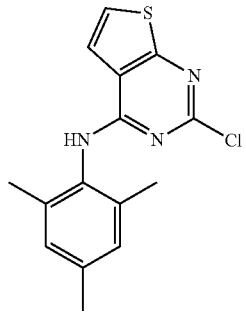

To a solution of 2,4-dichlorothieno[2,3-d]pyrimidine (805 mg, 3.94 mmol), TFA (0.91 mL, 11.82 mmol) in TFE (11 mL) was added 2,4,6-trimethylaniline (0.15 mg, 1.1 mmol) in a sealed tube. The reaction was stirred at 90° C. for 2 d. Reaction mixture was diluted with CH₂Cl₂ and washed with saturated NaHCO₃ (3×20 mL). The combined organic layers were washed with brine, dried over Na₂SO₄, filtered and concentrated in vacuo. The crude product was purified by HPLC to afford the product as a white solid (43.4 mg, 36%):

¹H NMR (DMSO, 300 MHz) δ 2.08 (s, 6H), 2.27 (s, 3H), 6.97 (s, 2H), 7.69 (d, J=6.0 Hz, 1H), 7.78 (d, J=6.0 Hz, 1H), 9.68 (s, 1H).

Example 8

4-(4-Mesitylamino)thieno[2,3-d]pyrimidin-2-ylamino)benzonitrile

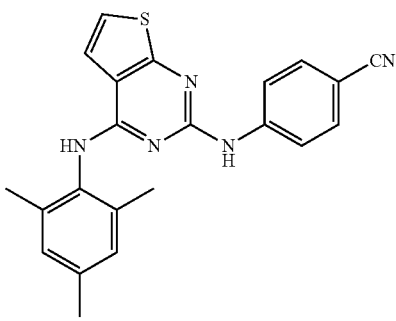

To a solution of 2-Chloro-N-mesitylthieno[2,3-d]pyrimidin-4-amine (43.4 mg, 0.14 mmol), TFA (0.09 mL, 1.14 mmol) in TFE (0.6 mL) was added 4-aminobenzonitrile (68 mg, 0.57 mmol) in a sealed tube. The reaction was stirred at 90° C. for 15 h. Reaction mixture was diluted with ethyl acetate and washed with saturated NaHCO₃ (3×10 mL). The combined organic layers were washed with brine, dried over Na₂SO₄, filtered and concentrated in vacuo. The crude product was purified by prep plate with Hexanes/ethyl acetate (2:1) as eluant to afford the product as a white solid (55.1 mg, 8%):

¹H NMR (DMSO, 300 MHz) δ 2.11 (s, 6H), 2.32 (s, 3H), 6.12 (s, 2H), 6.58 (d, J=8.4 Hz, 2H), 7.02 (d, J=6.0 Hz, 1H), 7.36 (d, J=8.4 Hz, 2H), 7.66 (d, J=6.0 Hz, 1H), 9.27 (s, 1H), 9.68 (s, 1H).

Scheme 2

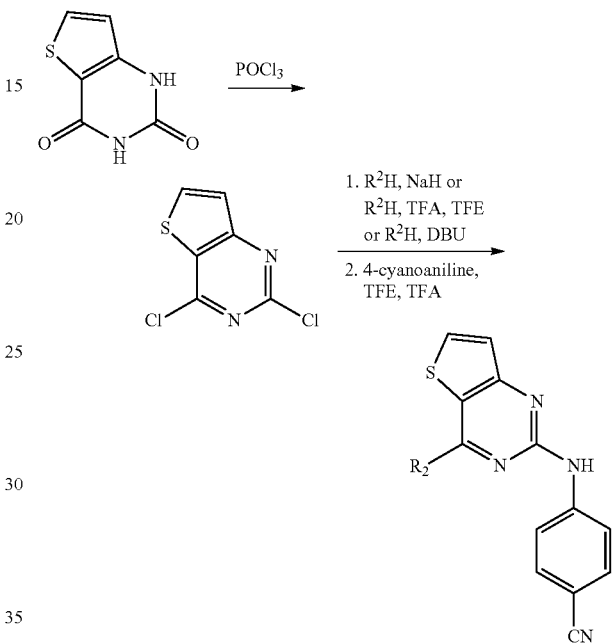

Chlorination of commercially available thieno[3,2-d]pyrimidine-2,4(1H,3H)-dione with phosphonyl chloride provided the dichloro-thienopyrimidine. R²H (defined as a substituted or unsubstituted aniline, a substituted or unsubstituted phenol or a substituted or unsubstituted thiophenol) was coupled on the ring system with trifluoroethanol and trifluoroacetic acid (when R²H is a substituted or unsubstituted aniline), sodium hydride (when R²H is a substituted or unsubstituted phenol), or DBU (when R²H is a substituted or unsubstituted thiophenol). 4-Aminobenzonitrile was coupled in the presence of trifluoroethanol and trifluoroacetic acid to provide a series of thieno[3,2-d]pyrimidine derivatives with various R² substitutions.

Example 9

2,4-Dichlorothieno[3,2-d]pyrimidine

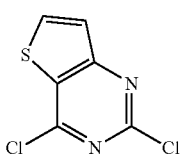

A mixture of thieno[3,2-d]pyrimidine-2,4(1H,3H)-dione (1.02 g, 6.07 mmol) and phosphonyl chloride (15 mL, 161 mmol) was heated at 116° C. for 5 h. Upon completion of the reaction, the reaction mixture was poured into ice and extract with ethyl acetate 3 times. The combined organic layers were washed with brine, dried over Na₂SO₄, filtered and concentrated in vacuo. Purification by column chromatography, eluting with Hexanes/Ethyl Acetate (9:1) afforded the product as a white solid (343 mg, 28%):

¹H NMR (DMSO, 300 MHz) δ 7.73 (d, J=5.4 Hz, 1H), 8.69 (d, J=5.7 Hz, 1H).

Example 10

2-Chloro-4-(mesityloxy)thieno[3,2-d]pyrimidine

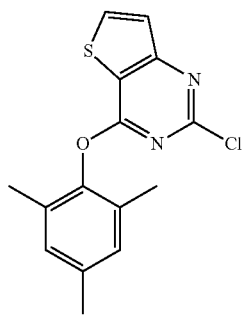

A stirred suspension of NaH (7.8 mg, 0.19 mmol) in dry THF (1 mL) was added 2,4,6-trimethyl phenol (26.4 mg, 0.19 mmol) and stirred at room temperature for 30 min under Argon. The reaction mixture was added to a solution of 2,4-dichlorothieno[3,2-d]pyrimidine (39.6 mg, 0.19 mmol) in dry THF (1 mL) at 0° C. and allow it to slowly warmed up to room temperature. After stirring the reaction for 4 h, the resulting mixture was diluted with water and washed with EtOAc. The combined organic layers were washed with water, brine, dried over Na₂SO₄, filtered and concentrated in vacuo. The crude product was purified by column chromatography, eluting with hexanes/ethyl acetate (9:1) to give the product as a white solid (32.4 mg, 56%):

¹H NMR (DMSO, 300 MHz) δ 2.0 (s, 6H), 2.27 (s, 3H), 6.98 (s, 2H), 7.68 (d, J=6.0 Hz, 1H), 7.97 (d, J=5.7 Hz, 1H).

Example 11

4-(4-(mesityloxy)thieno[3,2-d]pyrimidin-2-ylamino) benzonitrile

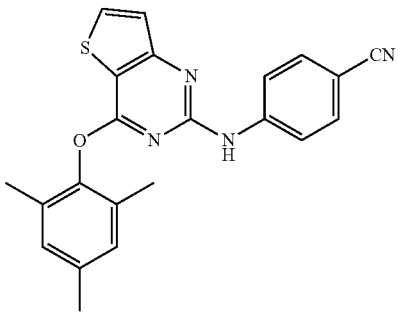

To a solution of 2-chloro-4-(mesityloxy)thieno[3,2-d]pyrimidine (32.4 mg, 0.11 mmol), TFA (0.13 mL, 1.71 mmol) in TFE (0.7 mL) was added 4-aminobenzonitrile (100 mg, 0.88 mmol) in a sealed tube. The reaction was stirred at 90° C. for 15 h. Reaction mixture was diluted with ethyl acetate (5 mL) and washed with saturated NaHCO₃ (3×10 mL). The combined organic layers were washed with brine, dried over Na₂SO₄, filtered and concentrated in vacuo. The crude product was purified by prep HPLC afforded the product as a white solid (26.7 mg, 63%):

¹H NMR (DMSO, 300 MHz) δ 2.05 (s, 6H), 2.27 (s, 3H), 7.02 (s, 2H), 7.37 (d, J=5.7 Hz, 1H), 7.40 (d, J=8.2 Hz, 2H), 7.59 (d, J=8.4 Hz, 2H), 8.27 (d, J=5.7 Hz, 1H), 10.05 (s, 1H).

Example 12

4-(2-Chlorothieno[3,2-d]pyrimidin-4-yloxy)-3,5-dimethylbenzonitrile

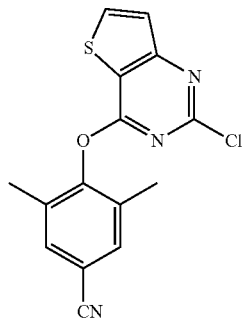

A stirred suspension of NaH (29.7 mg, 0.74 mmol) in dry NMP (3.5 mL) was added 4-hydroxy-3,5-dimethylbenzonitrile (108.2 mg, 0.74 mmol) and stirred at room temperature for 30 min under Argon. The reaction mixture was added to a solution of 2,4-dichlorothieno[3,2-d]pyrimidine (39.6 mg, 0.19 mmol) in dry NMP (4 mL) and heated at 50° C. for 5 h. The resulting mixture was diluted with water and washed with EtOAc. The combined organic layers were washed with water, brine, dried over Na₂SO₄, filtered and concentrated in vacuo. The crude product was purified by column chromatography, eluting with hexanes/ethyl acetate (4:1) to give the product as a white solid (189 mg, 81%):

¹H NMR (DMSO, 300 MHz) δ 2.11 (s, 6H), 7.68 (d, J=5.7 Hz, 1H), 7.76 (s, 2H), 8.59 (d, J=5.4 Hz, 1H).

Example 13

4-(2-(4-cyanophenylamino)thieno[3,2-d]pyrimidin-4-yloxy)-3,5-dimethylbenzonitrile

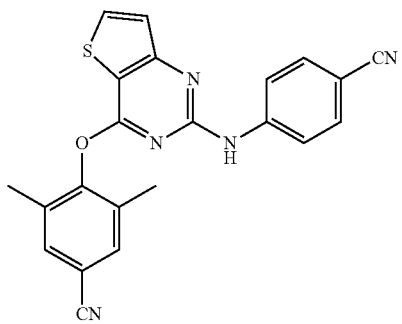

To a solution of 4-(2-chlorothieno[3,2-d]pyrimidin-4-yloxy)-3,5-dimethylbenzonitrile (187 mg, 0.6 mmol), TFA (0.37 mL, 4.8 mmol) in TFE (3 mL) was added 4-aminobenzonitrile (283 mg, 2.4 mmol) in a sealed tube. The reaction was stirred at 90° C. for 15 h. Reaction mixture was diluted with ethyl acetate (5 mL) and washed with saturated NaHCO$_3$ (3×10 mL). The combined organic layers were washed with brine, dried over Na$_2$SO$_4$, filtered and concentrated in vacuo. The crude product was purified by prep HPLC afforded the product as a white solid (81 mg, 34%):

$^1$H NMR (DMSO, 300 MHz) δ 2.16 (s, 6H), 7.47 (d, J=5.4 Hz, 1H), 7.53 (d, J=8.7 Hz, 2H), 7.68 (d, J=8.4 Hz, 2H), 7.80 (s, 2H), 8.40 (d, J=5.4 Hz, 1H), 10.06 (s, 1H).

Example 14

2-Chloro-N-mesitylthieno[3,2-d]pyrimidin-4-amine

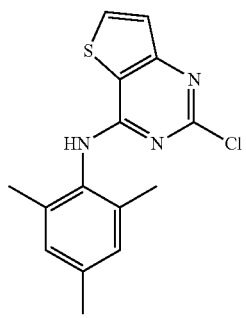

To a solution of 2,4-dichlorothieno[3,2-d]pyrimidine (148 mg, 0.73 mmol), TFA (0.17 mL, 2.19 mmol) in TFE (2 mL) was added 2,4,6-trimethylaniline (0.15 mg, 1.1 mmol) in a sealed tube. The reaction was stirred at 90° C. for 15 h. The reaction mixture was diluted with CH$_2$Cl$_2$ and washed with saturated NaHCO$_3$ solution (3×20 mL). The combined organic layers were washed with brine, dried over Na$_2$SO$_4$, filtered, and concentrated in vacuo. The crude product was purified by column chromatography eluting with Hexanes: ethyl acetate (4:1) to afford the product as a white solid (51.4 mg, 23%):

$^1$H NMR (DMSO, 300 MHz) δ 2.17 (s, 6H), 2.37 (s, 3H), 6.76, (d, J=5.7 Hz, 1H), 6.94 (broad s, 1H), 6.99 (s, 2H), 7.6 (d, J=5.7 Hz, 1H).

Example 15

4-(4-(mesitylamino)thieno[3,2-d]pyrimidin-2-ylamino)benzonitrile

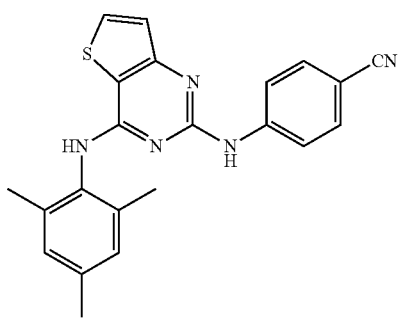

To a solution of 2-Chloro-N-mesitylthieno[3,2-d]pyrimidin-4-amine (51.4 mg, 0.17 mmol), TFA (0.11 mL, 1.36 mmol) in TFE (1 mL) was added 4-aminobenzonitrile (80.2 mg, 0.68 mmol) in a sealed tube. The reaction was stirred at 90° C. for 15 h. Reaction mixture was diluted with ethyl acetate and washed with saturated NaHCO$_3$ (3×10 mL). The combined organic layers were washed with brine, dried over Na$_2$SO$_4$, filtered and concentrated in vacuo. The crude product was purified by prep HPLC to afford the product as a white solid (13 mg, 20%): $^1$H NMR (DMSO, 300 MHz) δ 2.09 (s, 6H), 2.31 (s, 3H), 7.00 (s, 2H), 7.28 (d, J=5.7 Hz, 1H), 7.66 (d, J=8.4 Hz, 2H), 8.06-8.08 (m, 3H), 9.60 (bs, 1H), 9.72 (bs, 1H).

Scheme 3

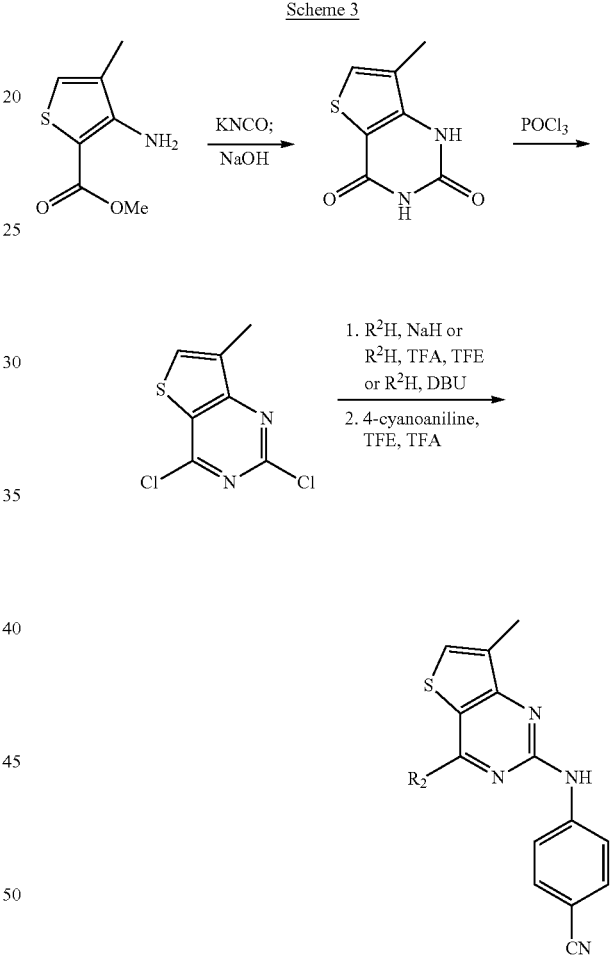

Starting with commercially available methyl-3-amino-4-methylthiophene-2-carboxylate and cyclized to thieno[3,2]pyrimidine by first treating with potassium cyanate followed by refluxing in 6% aqueous sodium hydroxide solution. Chlorination with phosphonyl chloride provided the dichlorothienopyrimidine. R$^2$H (defined as above) was coupled on the ring system with trifluoroethanol and trifluoroacetic acid (when R$^2$H is a substituted or unsubstituted aniline), sodium hydride (when R$^2$H is a substituted or unsubstituted phenol), or DBU (when R$^2$H is a substituted or unsubstituted thiophenol). 4-Aminobenzonitrile was coupled in the presence of trifluoroethanol and trifluoroacetic acid to provide a series of 7-methylthieno[3,2-d]pyrimidine compounds with various R² substitutions.

Example 16

7-Methylthieno[3,2-d]pyrimidine-2,4(1H,3H)-dione

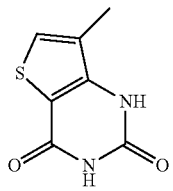

To a stirred solution of methyl-3-amino-4-methylthiophene-2-carboxylate (530 mg, 3.1 mmol) in acetic acid (15.5 mL) and water (1.6 mL) was added a solution of potassium cyanate (754 mg, 9.3 mmol) dissolved in water (2.5 mL) dropwise via syringe. The reaction was stirred at room temperature for 15 h, upon completion of the reaction; the reaction mixture was concentrated to 75% and filtered off white solid. To the solid was added 6% aqueous sodium hydroxide (16 mL) and refluxed for 2 h. After cooling to room temperature, the solution was acidified using 12N HCl to pH=6. The resultant precipitate was filtered, washed with water and dried in vacuum oven overnight to give 403 mg (71%) of the title compound as a white solid which was used without any further purification:

¹H NMR (DMSO, 300 MHz) δ 2.17 (s, 3H), 7.67 (s, 1H), 11.21 (bs, 1H), 11.4 (bs, 1H).

Example 17

2,4-Dichloro-7-methylthieno [3,2-d]pyrimidine

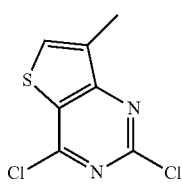

A mixture of 7-methylthieno[3,2-d]pyrimidine-2,4(1H,3H)-dione (403 mg, 2.21 mmol) and phosphonyl chloride (8.0 mL, 86 mmol) was heated at 116° C. for 4 h. Upon completion of the reaction, the reaction mixture was poured onto ice and extracted with ethyl acetate 3 times. The combined organic layers were washed with brine, dried over Na₂SO₄, filtered and concentrated in vacuo. Purification by column chromatography, eluting with Hexanes/Ethyl Acetate (5:1) afforded the product as a white solid (145 mg, 88%):

¹H NMR (DMSO, 300 MHz) δ 2.39 (s, 3H), 8.34 (s, 1H).

Example 18

2-Chloro-4-(mesityloxy)-7-methylthieno [3,2-d]pyrimidine

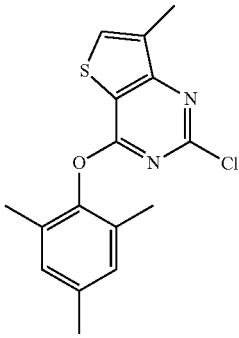

A stirred suspension of NaH (16 mg, 0.4 mmol) in dry THF (2 mL) was added 2,4,6-trimethyl phenol and stirred at room temperature for 30 min under argon. The reaction mixture was added to a solution of 2,4-ichloro-7-methylthieno[3,2-d]pyrimidine (87 mg, 0.4 mmol) in dry THF (2 mL) at 0° C. and slowly warmed up to room temperature. After stirring the reaction for 2 h, the resulting mixture was diluted with water and washed with EtOAc. The combined organic layers were washed with water, brine, dried over Na₂SO₄, filtered and concentrated in vacuo. The crude product was purified by column chromatography, eluting with hexanes/ethyl acetate (2:1) to give the product as a white solid (136 mg, 90%):

¹H NMR (DMSO, 300 MHz) δ 2.0 (s, 3H), 2.08 (s, 6H), 2.37 (s, 3H), 6.99 (s, 2H), 7.87 (s, 1H).

Example 19

4-(4-Mesityloxy)-7-methylthieno[3,2-d]pyrimidin-2-ylamino)benzonitrile

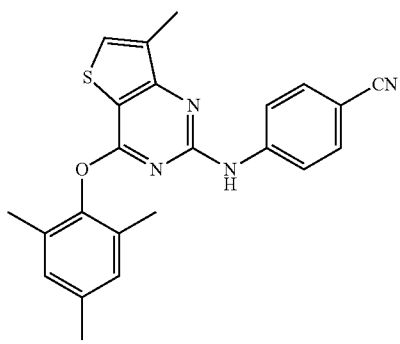

To a solution of 2-chloro-4-(mesityloxy)-7-methylthieno [3,2-d]pyrimidine (136 mg, 0.43 mmol), TFA (0.26 mL, 3.42 mmol) in TFE (1.43 mL) was added 4-aminobenzonitrile (202 mg, 1.71 mmol) in a sealed tube. The reaction was stirred at 90° C. for 15 h. Reaction mixture was diluted with ethyl acetate (5 mL) and washed with saturated NaHCO₃ (3×10 mL). The combined organic layers were washed with brine, dried over Na₂SO₄, filtered, and concentrated in vacuo. The crude product was purified by prep plate, eluting with hexanes/ethyl acetate (2:1) to give the product as a white solid (7.6 mg, 5.3%):

$^1$H NMR (DMSO, 300 MHz) δ 2.0s (s, 6H), 2.31 (s, 3H), 2.37 (s, 3H), 7.02 (s, 2H), 7.49 (d, J=8.7 Hz, 2H), 7.74 (d, J=8.7 Hz, 2H), 7.98 (s, 1H), 10.06 (s, 1H).

II. Biological Activity

Example 20

Inhibition of HIV-1 Reverse Transcriptase

Numerous compounds were screened for inhibitory activity against human immunodeficiency virus type 1 (HIV-1) using a high throughput cell-based assay using HIV-1 expressing firefly luciferase as a reporter gene and pseudotyped with vesicular stomatitis virus envelope glycoprotein (VSV-G). Experimental procedures were essentially as described by Connor et al. in *Journal of Virology* (1996), 70: 5306-5311 (Characterization of the functional properties of env genes from long-term survivors of human immunodeficiency virus type 1 infection), and Popik et al. in *Journal of Virology* (2002), 76: 4709-4722 (Human immunodeficiency virus type 1 uses lipid raft-co-localized CD4 and chemokine receptors for productive entry into CD4+ T cells). It should be particularly appreciated that the virus contains two introduced mutations in the RT gene (K103N and Y181C, created by PCR mutagenesis) that render the virus highly resistant to current non-nucleoside HIV-1 drugs. Virus stocks were generated by cotransfection of plasmid DNA encoding VSV-G with vector pNL4-3Env(−)Luc(+) into 293T cells. Sixty-four hours after transfection, virus-containing medium was collected by centrifugation and stored frozen at −80° C.

HeLa cells were infected with the VSV-G pseudotyped virus in the presence of screening compounds in a 384-well microtiter plate format. Forty-eight hours after initial infection, lysis buffer and Luciferase Assay Reagent (Promega) was added to the cells and luciferase activity was determined by counting the resultant luminescence using a LJL luminometer. Since the luciferase gene is carried in the virus genome, its expression level directly reflects the virus replication level in the presence of a compound.

To evaluate the activity of the compounds against wild type HIV-1, the HeLa-JC53 cell line that expresses high levels of CD4 and CCR5 (see e.g., Platt et al. in *Journal of Virology* (1998), 72: 2855-2864: Effect of CCR5 and CD4 cell surface concentrations on infection by macrophagetropic isolates of human immunodeficiency virus type 1) was modified by isolation of a stable cell line that expresses luciferase under the control of the HIV-1 promoter (long terminal repeat, i.e., LTR). HIV-1 infection of this cell line stimulates the transcription of luciferase from the HIV-1 promoter and the luciferase gene expression level is proportional to the level of virus replication (Harrington et al. in *Journal of Virology Methods* (2000), 88: 111-115: Direct detection of infection of HIV-1 in blood using a centrifugation-indicator cell assay; and Roos et al. in *Virology* (2000), 273: 307-315: LuSIV cells: a reporter cell line for the detection and quantitation of a single cycle of HIV and SIV replication). Procedures for virus infection, compound testing and luciferase activity determination were the same as for the VSV-G pseudotyped HIV-1.

Two approaches were used to evaluate the cytotoxicity of the positive compounds discovered in the HIV-1 virus assays. The first approach employed another modified HeLa-JC53 cell line that constitutively expresses high level of luciferase without virus infection. The level of luciferase expression in these cells served as an indicator for cell replication in the presence of the compounds. Procedures for compound testing and luciferase activity determination were the same as for the virus infection tests. The other toxicity assay utilized HeLe-JC53 cells and a commercially available MTS assay kit (Promega) that measures the mitochondria function of the cells.

Results

The results are listed below 1 as $EC_{50}$ (nM) and $IC_{50}$ (nM). Table legend: A is <10, B is between 10 and 100, C is >100, ND is not determined Note that many compounds of this invention exhibit activities on wild-type (WT) and resistant mutants below 10 nM.

| Cpd | Structure | $EC_{50}$ WT (nM) | $EC_{50}$ Y181C (nM) | $EC_{50}$ Y188L (nM) | $EC_{50}$ L100I-K103N (nM) |
| --- | --- | --- | --- | --- | --- |
| 1 | (structure shown; CLogP: 7.00733) | A | A | A | B |

-continued

| Cpd | Structure | EC$_{50}$ WT (nM) | EC$_{50}$ Y181C (nM) | EC$_{50}$ Y188L (nM) | EC$_{50}$ L100I-K103N (nM) |
|---|---|---|---|---|---|
| 2 | (structure; CLogP: 7.71933) | A | B | C | C |
| 3 | (structure; CLogP: 5.94133) | A | B | A | A |
| 4 | (structure; CLogP: 6.79733) | A | B | B | B |
| 5 | (structure; CLogP: 8.36933) | B | C | C | C |

-continued

| Cpd | Structure | EC$_{50}$ WT (nM) | EC$_{50}$ Y181C (nM) | EC$_{50}$ Y188L (nM) | EC$_{50}$ L100I-K103N (nM) |
|---|---|---|---|---|---|
| 6 | CLogP: 7.50633 | B | B | B | B |
| 7 | CLogP: 5.73133 | A | A | A | B |
| 8 | CLogP: 8.21837 | A | B | B | ND |
| 9 | CLogP: 6.44033 | A | A | A | A |

Contemplated Compounds and Prophetic Examples

In addition to the examples listed above, this invention provides or contemplates many compounds, examples of which are shown in the tables that follow.

TABLE 1

Contemplated Compounds of Formula IA-1

IA-1

| | Ar | Z |
|---|---|---|
| 1. | o,o'-diCH$_3$O-p-(CH=CHCN)phenyl | CH$_3$ |
| 2. | o,o'-diCH$_3$O-p-(CH=CHCN)phenyl | H |
| 3. | o,o'-diCH$_3$O-p-(CH=CHCN)phenyl | Br |
| 4. | o,o'-diCH$_3$O-p-(CH=CHCN)phenyl | CH$_2$CH$_3$ |
| 5. | o,o'-diCH$_3$O-p-(CH=CHCN)phenyl | isopropyl |
| 6. | o,o'-diCH$_3$O-p-(CH=CHCN)phenyl | cyclopropyl |
| 7. | o,o'-diCH$_3$O-p-(CH=CHCN)phenyl | F |
| 8. | o,o'-diCH$_3$O-p-(CH=CHCN)phenyl | Cl |
| 9. | o,o'-diCH$_3$O-p-(CH=CHCN)phenyl | CF$_3$ |
| 10. | o,o'-diCH$_3$O-p-(CH=CHCN)phenyl | OCH$_3$ |
| 11. | o,o'-diCH$_3$-p-(CH=CHCN)phenyl | CH$_3$ |
| 12. | o,o'-diCH$_3$-p-(CH=CHCN)phenyl | H |
| 13. | o,o'-diCH$_3$-p-(CH=CHCN)phenyl | Br |
| 14. | o,o'-diCH$_3$-p-(CH=CHCN)phenyl | CH$_2$CH$_3$ |
| 15. | o,o'-diCH$_3$-p-(CH=CHCN)phenyl | isopropyl |
| 16. | o,o'-diCH$_3$-p-(CH=CHCN)phenyl | cyclopropyl |
| 17. | o,o'-diCH$_3$-p-(CH=CHCN)phenyl | F |
| 18. | o,o'-diCH$_3$-p-(CH=CHCN)phenyl | Cl |
| 19. | o,o'-diCH$_3$-p-(CH=CHCN)phenyl | CF$_3$ |
| 20. | o,o'-diCH$_3$-p-(CH=CHCN)phenyl | OCH$_3$ |
| 21. | o,o'-di-CH$_3$O-p-CN-phenyl | CH$_3$ |
| 22. | o,o'-di-CH$_3$O-p-CN-phenyl | H |
| 23. | o,o'-di-CH$_3$O-p-CN-phenyl | Br |
| 24. | o,o'-di-CH$_3$O-p-CN-phenyl | CH$_2$CH$_3$ |
| 25. | o,o'-di-CH$_3$O-p-CN-phenyl | isopropyl |
| 26. | o,o'-di-CH$_3$O-p-CN-phenyl | cyclopropyl |
| 27. | o,o'-di-CH$_3$O-p-CN-phenyl | F |
| 28. | o,o'-di-CH$_3$O-p-CN-phenyl | Cl |
| 29. | o,o'-di-CH$_3$O-p-CN-phenyl | CF$_3$ |
| 30. | o,o'-di-CH$_3$O-p-CN-phenyl | OCH$_3$ |
| 31. | 4-cyclopropylnaphth-1-yl | CH$_3$ |
| 32. | 4-cyclopropylnaphth-1-yl | H |
| 33. | 4-cyclopropylnaphth-1-yl | Br |
| 34. | 4-cyclopropylnaphth-1-yl | CH$_2$CH$_3$ |
| 35. | 4-cyclopropylnaphth-1-yl | isopropyl |
| 36. | 4-cyclopropylnaphth-1-yl | cyclopropyl |
| 37. | 4-cyclopropylnaphth-1-yl | F |
| 38. | 4-cyclopropylnaphth-1-yl | Cl |
| 39. | 4-cyclopropylnaphth-1-yl | CF$_3$ |
| 40. | 4-cyclopropylnaphth-1-yl | OCH$_3$ |
| 41. | 2-CH$_3$-4-cyclopropylnaphth-1-yl | CH$_3$ |
| 42. | 2-CH$_3$-4-cyclopropylnaphth-1-yl | H |
| 43. | 2-CH$_3$-4-cyclopropylnaphth-1-yl | Br |
| 44. | 2-CH$_3$-4-cyclopropylnaphth-1-yl | CH$_2$CH$_3$ |
| 45. | 2-CH$_3$-4-cyclopropylnaphth-1-yl | isopropyl |
| 46. | 2-CH$_3$-4-cyclopropylnaphth-1-yl | cyclopropyl |
| 47. | 2-CH$_3$-4-cyclopropylnaphth-1-yl | F |
| 48. | 2-CH$_3$-4-cyclopropylnaphth-1-yl | Cl |
| 49. | 2-CH$_3$-4-cyclopropylnaphth-1-yl | CF$_3$ |
| 50. | 2-CH$_3$-4-cyclopropylnaphth-1-yl | OCH$_3$ |
| 51. | o,o'-di-CH$_3$-p-CN-phenyl | CH$_3$ |
| 52. | o,o'-di-CH$_3$-p-CN-phenyl | H |
| 53. | o,o'-di-CH$_3$-p-CN-phenyl | Br |
| 54. | o,o'-di-CH$_3$-p-CN-phenyl | CH$_2$CH$_3$ |
| 55. | o,o'-di-CH$_3$-p-CN-phenyl | isopropyl |
| 56. | o,o'-di-CH$_3$-p-CN-phenyl | cyclopropyl |
| 57. | o,o'-di-CH$_3$-p-CN-phenyl | F |
| 58. | o,o'-di-CH$_3$-p-CN-phenyl | Cl |
| 59. | o,o'-di-CH$_3$-p-CN-phenyl | CF$_3$ |
| 60. | o,o'-di-CH$_3$-p-CN-phenyl | OCH$_3$ |
| 61. | 2,4,6-trimethyl phenyl | CH$_3$ |
| 62. | 2,4,6-trimethyl phenyl | H |
| 63. | 2,4,6-trimethyl phenyl | Br |
| 64. | 2,4,6-trimethyl phenyl | CH$_2$CH$_3$ |
| 65. | 2,4,6-trimethyl phenyl | isopropyl |
| 66. | 2,4,6-trimethyl phenyl | cyclopropyl |
| 67. | 2,4,6-trimethyl phenyl | F |
| 68. | 2,4,6-trimethyl phenyl | Cl |
| 69. | 2,4,6-trimethyl phenyl | CF$_3$ |
| 70. | 2,4,6-trimethyl phenyl | OCH$_3$ |
| 71. | 2-CH$_3$-4-cyclopropyl phenyl | CH$_3$ |
| 72. | 2-CH$_3$-4-cyclopropyl phenyl | H |
| 73. | 2-CH$_3$-4-cyclopropyl phenyl | Br |
| 74. | 2-CH$_3$-4-cyclopropyl phenyl | CH$_2$CH$_3$ |
| 75. | 2-CH$_3$-4-cyclopropyl phenyl | isopropyl |
| 76. | 2-CH$_3$-4-cyclopropyl phenyl | cyclopropyl |
| 77. | 2-CH$_3$-4-cyclopropyl phenyl | F |
| 78. | 2-CH$_3$-4-cyclopropyl phenyl | Cl |
| 79. | 2-CH$_3$-4-cyclopropyl phenyl | CF$_3$ |
| 80. | 2-CH$_3$-4-cyclopropyl phenyl | OCH$_3$ |
| 81. | 2-Cl-4-cyclopropyl phenyl | CH$_3$ |
| 82. | 2-Cl-4-cyclopropyl phenyl | H |
| 83. | 2-Cl-4-cyclopropyl phenyl | Br |
| 84. | 2-Cl-4-cyclopropyl phenyl | CH$_2$CH$_3$ |
| 85. | 2-Cl-4-cyclopropyl phenyl | isopropyl |
| 86. | 2-Cl-4-cyclopropyl phenyl | cyclopropyl |
| 87. | 2-Cl-4-cyclopropyl phenyl | F |
| 88. | 2-Cl-4-cyclopropyl phenyl | Cl |
| 89. | 2-Cl-4-cyclopropyl phenyl | CF$_3$ |
| 90. | 2-Cl-4-cyclopropyl phenyl | OCH$_3$ |
| 91. | 2,6-di-CH$_3$-4-cyclopropyl phenyl | CH$_3$ |
| 92. | 2,6-di-CH$_3$-4-cyclopropyl phenyl | H |
| 93. | 2,6-di-CH$_3$-4-cyclopropyl phenyl | Br |
| 94. | 2,6-di-CH$_3$-4-cyclopropyl phenyl | CH$_2$CH$_3$ |
| 95. | 2,6-di-CH$_3$-4-cyclopropyl phenyl | isopropyl |
| 96. | 2,6-di-CH$_3$-4-cyclopropyl phenyl | cyclopropyl |
| 97. | 2,6-di-CH$_3$-4-cyclopropyl phenyl | F |
| 98. | 2,6-di-CH$_3$-4-cyclopropyl phenyl | Cl |
| 99. | 2,6-di-CH$_3$e-4-cyclopropyl phenyl | CF$_3$ |
| 100. | 2,6-di-CH$_3$-4-cyclopropyl phenyl | OCH$_3$ |
| 101. | o,o'-di-CH$_3$-p-acetyl-phenyl | CH$_3$ |
| 102. | o,o'-di-CH$_3$-p-acetyl-phenyl | H |
| 103. | o,o'-di-CH$_3$-p-acetyl-phenyl | Br |
| 104. | o,o'-di-CH$_3$-p-acetyl-phenyl | CH$_2$CH$_3$ |
| 105. | o,o'-di-CH$_3$-p-acetyl-phenyl | isopropyl |
| 106. | o,o'-di-CH$_3$-p-acetyl-phenyl | cyclopropyl |
| 107. | o,o'-di-CH$_3$-p-acetyl-phenyl | F |
| 108. | o,o'-di-CH$_3$-p-acetyl-phenyl | Cl |
| 109. | o,o'-di-CH$_3$-p-acetyl-phenyl | CF$_3$ |
| 110. | o,o'-di-CH$_3$-p-acetyl-phenyl | OCH$_3$ |

TABLE 2

Contemplated Compounds of Formula IA-2

IA-2

| | Ar | W |
|---|---|---|
| 111. | o,o'-diCH$_3$O-p-(CH=CHCN)phenyl | CH$_3$ |
| 112. | o,o'-diCH$_3$O-p-(CH=CHCN)phenyl | H |
| 113. | o,o'-diCH$_3$O-p-(CH=CHCN)phenyl | Br |
| 114. | o,o'-diCH$_3$O-p-(CH=CHCN)phenyl | CH$_2$CH$_3$ |
| 115. | o,o'-diCH$_3$O-p-(CH=CHCN)phenyl | isopropyl |
| 116. | o,o'-diCH$_3$O-p-(CH=CHCN)phenyl | cyclopropyl |
| 117. | o,o'-diCH$_3$O-p-(CH=CHCN)phenyl | F |
| 118. | o,o'-diCH$_3$O-p-(CH=CHCN)phenyl | Cl |
| 119. | o,o'-diCH$_3$O-p-(CH=CHCN)phenyl | CF$_3$ |
| 120. | o,o'-diCH$_3$O-p-(CH=CHCN)phenyl | OCH$_3$ |
| 121. | o,o'-diCH$_3$-p-(CH=CHCN)phenyl | CH$_3$ |
| 122. | o,o'-diCH$_3$-p-(CH=CHCN)phenyl | H |
| 123. | o,o'-diCH$_3$-p-(CH=CHCN)phenyl | Br |
| 124. | o,o'-diCH$_3$-p-(CH=CHCN)phenyl | CH$_2$CH$_3$ |
| 125. | o,o'-diCH$_3$-p-(CH=CHCN)phenyl | isopropyl |
| 126. | o,o'-diCH$_3$-p-(CH=CHCN)phenyl | cyclopropyl |
| 127. | o,o'-diCH$_3$-p-(CH=CHCN)phenyl | F |
| 128. | o,o'-diCH$_3$-p-(CH=CHCN)phenyl | Cl |
| 129. | o,o'-diCH$_3$-p-(CH=CHCN)phenyl | CF$_3$ |
| 130. | o,o'-diCH$_3$-p-(CH=CHCN)phenyl | OCH$_3$ |
| 131. | o,o'-di-CH$_3$O-p-CN-phenyl | CH$_3$ |
| 132. | o,o'-di-CH$_3$O-p-CN-phenyl | H |
| 133. | o,o'-di-CH$_3$O-p-CN-phenyl | Br |
| 134. | o,o'-di-CH$_3$O-p-CN-phenyl | CH$_2$CH$_3$ |
| 135. | o,o'-di-CH$_3$O-p-CN-phenyl | isopropyl |
| 136. | o,o'-di-CH$_3$O-p-CN-phenyl | cyclopropyl |
| 137. | o,o'-di-CH$_3$O-p-CN-phenyl | F |
| 138. | o,o'-di-CH$_3$O-p-CN-phenyl | Cl |
| 139. | o,o'-di-CH$_3$O-p-CN-phenyl | CF$_3$ |
| 140. | o,o'-di-CH$_3$O-p-CN-phenyl | OCH$_3$ |
| 141. | 4-cyclopropylnaphth-1-yl | CH$_3$ |
| 142. | 4-cyclopropylnaphth-1-yl | H |
| 143. | 4-cyclopropylnaphth-1-yl | Br |
| 144. | 4-cyclopropylnaphth-1-yl | CH$_2$CH$_3$ |
| 145. | 4-cyclopropylnaphth-1-yl | isopropyl |
| 146. | 4-cyclopropylnaphth-1-yl | cyclopropyl |
| 147. | 4-cyclopropylnaphth-1-yl | F |
| 148. | 4-cyclopropylnaphth-1-yl | Cl |
| 149. | 4-cyclopropylnaphth-1-yl | CF$_3$ |
| 150. | 4-cyclopropylnaphth-1-yl | OCH$_3$ |
| 151. | 2-CH$_3$-4-cyclopropylnaphth-1-yl | CH$_3$ |
| 152. | 2-CH$_3$-4-cyclopropylnaphth-1-yl | H |
| 153. | 2-CH$_3$-4-cyclopropylnaphth-1-yl | Br |
| 154. | 2-CH$_3$-4-cyclopropylnaphth-1-yl | CH$_2$CH$_3$ |
| 155. | 2-CH$_3$-4-cyclopropylnaphth-1-yl | isopropyl |
| 156. | 2-CH$_3$-4-cyclopropylnaphth-1-yl | cyclopropyl |
| 157. | 2-CH$_3$-4-cyclopropylnaphth-1-yl | F |
| 158. | 2-CH$_3$-4-cyclopropylnaphth-1-yl | Cl |
| 159. | 2-CH$_3$-4-cyclopropylnaphth-1-yl | CF$_3$ |
| 160. | 2-CH$_3$-4-cyclopropylnaphth-1-yl | OCH$_3$ |
| 161. | o,o'-di-CH$_3$-p-CN-phenyl | CH$_3$ |
| 162. | o,o'-di-CH$_3$-p-CN-phenyl | H |
| 163. | o,o'-di-CH$_3$-p-CN-phenyl | Br |
| 164. | o,o'-di-CH$_3$-p-CN-phenyl | CH$_2$CH$_3$ |
| 165. | o,o'-di-CH$_3$-p-CN-phenyl | isopropyl |
| 166. | o,o'-di-CH$_3$-p-CN-phenyl | cyclopropyl |
| 167. | o,o'-di-CH$_3$-p-CN-phenyl | F |
| 168. | o,o'-di-CH$_3$-p-CN-phenyl | Cl |
| 169. | o,o'-di-CH$_3$-p-CN-phenyl | CF$_3$ |
| 170. | o,o'-di-CH$_3$-p-CN-phenyl | OCH$_3$ |
| 171. | 2,4,6-trimethyl phenyl | CH$_3$ |
| 172. | 2,4,6-trimethyl phenyl | H |
| 173. | 2,4,6-trimethyl phenyl | Br |
| 174. | 2,4,6-trimethyl phenyl | CH$_2$CH$_3$ |
| 175. | 2,4,6-trimethyl phenyl | isopropyl |
| 176. | 2,4,6-trimethyl phenyl | cyclopropyl |
| 177. | 2,4,6-trimethyl phenyl | F |
| 178. | 2,4,6-trimethyl phenyl | Cl |
| 179. | 2,4,6-trimethyl phenyl | CF$_3$ |
| 180. | 2,4,6-trimethyl phenyl | OCH$_3$ |
| 181. | 2-CH$_3$-4-cyclopropyl phenyl | CH$_3$ |
| 182. | 2-CH$_3$-4-cyclopropyl phenyl | H |
| 183. | 2-CH$_3$-4-cyclopropyl phenyl | Br |
| 184. | 2-CH$_3$-4-cyclopropyl phenyl | CH$_2$CH$_3$ |
| 185. | 2-CH$_3$-4-cyclopropyl phenyl | isopropyl |
| 186. | 2-CH$_3$-4-cyclopropyl phenyl | cyclopropyl |
| 187. | 2-CH$_3$-4-cyclopropyl phenyl | F |
| 188. | 2-CH$_3$-4-cyclopropyl phenyl | Cl |
| 189. | 2-CH$_3$-4-cyclopropyl phenyl | CF$_3$ |
| 190. | 2-CH$_3$-4-cyclopropyl phenyl | OCH$_3$ |
| 191. | 2-Cl-4-cyclopropyl phenyl | CH$_3$ |
| 192. | 2-Cl-4-cyclopropyl phenyl | H |
| 193. | 2-Cl-4-cyclopropyl phenyl | Br |
| 194. | 2-Cl-4-cyclopropyl phenyl | CH$_2$CH$_3$ |
| 195. | 2-Cl-4-cyclopropyl phenyl | isopropyl |
| 196. | 2-Cl-4-cyclopropyl phenyl | cyclopropyl |
| 197. | 2-Cl-4-cyclopropyl phenyl | F |
| 198. | 2-Cl-4-cyclopropyl phenyl | Cl |
| 199. | 2-Cl-4-cyclopropyl phenyl | CF$_3$ |
| 200. | 2-Cl-4-cyclopropyl phenyl | OCH$_3$ |
| 201. | 2,6-di-CH$_3$-4-cyclopropyl phenyl | CH$_3$ |
| 202. | 2,6-di-CH$_3$-4-cyclopropyl phenyl | H |
| 203. | 2,6-di-CH$_3$-4-cyclopropyl phenyl | Br |
| 204. | 2,6-di-CH$_3$-4-cyclopropyl phenyl | CH$_2$CH$_3$ |
| 205. | 2,6-di-CH$_3$-4-cyclopropyl phenyl | isopropyl |
| 206. | 2,6-di-CH$_3$-4-cyclopropyl phenyl | cyclopropyl |
| 207. | 2,6-di-CH$_3$-4-cyclopropyl phenyl | F |
| 208. | 2,6-di-CH$_3$-4-cyclopropyl phenyl | Cl |
| 209. | 2,6-di-CH$_3$4-cyclopropyl phenyl | CF$_3$ |
| 210. | 2,6-di-CH$_3$-4-cyclopropyl phenyl | OCH$_3$ |
| 211. | o,o'-di-CH$_3$-p-acetyl-phenyl | CH$_3$ |
| 212. | o,o'-di-CH$_3$-p-acetyl-phenyl | H |
| 213. | o,o'-di-CH$_3$-p-acetyl-phenyl | Br |
| 214. | o,o'-di-CH$_3$-p-acetyl-phenyl | CH$_2$CH$_3$ |
| 215. | o,o'-di-CH$_3$-p-acetyl-phenyl | isopropyl |
| 216. | o,o'-di-CH$_3$-p-acetyl-phenyl | cyclopropyl |
| 217. | o,o'-di-CH$_3$-p-acetyl-phenyl | F |
| 218. | o,o'-di-CH$_3$-p-acetyl-phenyl | Cl |
| 219. | o,o'-di-CH$_3$-p-acetyl-phenyl | CF$_3$ |
| 220. | o,o'-di-CH$_3$-p-acetyl-phenyl | OCH$_3$ |

What is claimed is:

1. A compound of formula

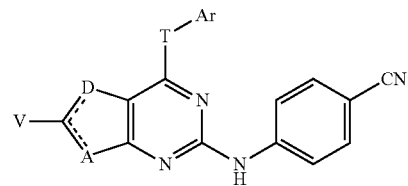

wherein:
the dashed line represents a double bond located between C(V) and D;
A is S;
D is C(W);
T is NH, O, or S;
W is H, F, Cl, Br, $C_1$-$C_6$ alkyl, $C_2$-$C_6$ alkenyl, $OC_1$-$C_6$ alkyl, $C_3$-$C_6$ cycloalkyl, $OC_3$-$C_6$ cycloalkyl, phenyl or benzyl; wherein the alkyl, alkenyl, cycloalkyl, phenyl groups and the phenyl moiety of the benzyl group are optionally substituted with 1-3 groups selected from halogen, $CF_3$, $C_1$-$C_3$ alkyl, and $OC_1$-$C_3$ alkyl;
V is H, halogen, or $C_1$-$C_6$ alkyl;
Ar is selected from (a), (b), (c), and (d) below:

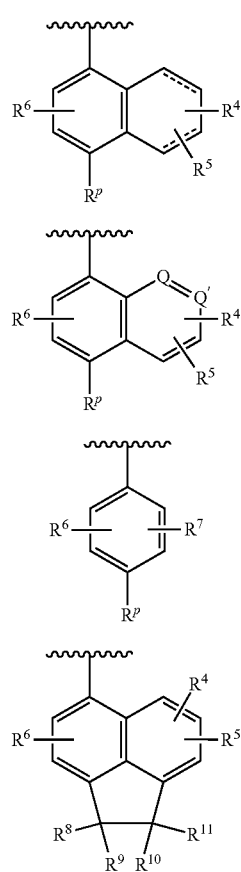

(a)

(b)

(c)

(d)

wherein:
each $R^P$ is selected from methyl, ethyl, propyl, isopropyl, cyclopropylmethyl, $C_3$-$C_6$ cycloalkyl, cyano, CH=CHCN, Cl, Br, I, acetyl, and $C_1$-$C_6$ alkyl-NH;
$R^4$, $R^5$, and $R^6$ are independently selected from H, F, Cl, Br, $CH_3$, $CF_3$, $CH_2F$, $CHF_2$, isopropyl, cyclopropyl, $OCH_3$, OH, $OCF_3$, $NH_2$ and $NHCH_3$;
or $R^6$ and $R^P$ on adjacent ring atoms, together with the ring atoms to which they are attached, form an additional fused five-membered ring;
Q and Q' are independently selected from N and CH;
$R^7$ is Cl, Br, I, $CH_3$, $CF_3$, $OCH_3$, isopropyl, cyclopropyl, t-butyl, or cyclobutyl; and
$R^8$, $R^9$, $R^{10}$, and $R^{11}$ are each, independently, H or $CH_3$;
or a pharmaceutically acceptable salt thereof.

2. The compound of claim 1, wherein Ar is (a) or (c).

3. The compound of claim 2, wherein $R^6$ is H or a substituent in the 2-position.

4. The compound of claim 3, wherein Ar is selected from 4-cyclopropyl phenyl; 4-cyclopropylmethyl phenyl; 4-bromophenyl; 2-chloro-4-bromophenyl; 4-bromo-1-naphthyl; 4-cyclopropyl-1-naphthyl; 2,6-dimethyl-4-cyanophenyl; 2,6-dimethoxy-4-cyanophenyl; 2,6-dimethyl-4-(2-cyanoethenyl) phenyl; 2,6-dimethoxy-4-(2-cyanoethenyl) phenyl; 2-methyl-4-cyclopropyl phenyl; 2,6-dimethyl-4-cyclopropyl phenyl; 2,6-di-trifluoromethyl-4-cyclopropyl phenyl; 2,4,6-trimethyl phenyl; and 2,6-dimethyl-4-acetyl phenyl.

5. The compound of claim 1, which is a compound of formula IA-2:

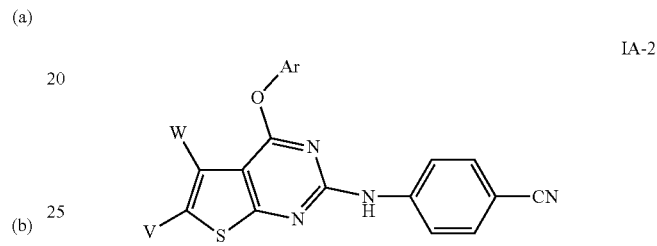

IA-2 or a pharmaceutically acceptable salt thereof.

6. The compound of claim 1, which is a compound of formula IA-4:

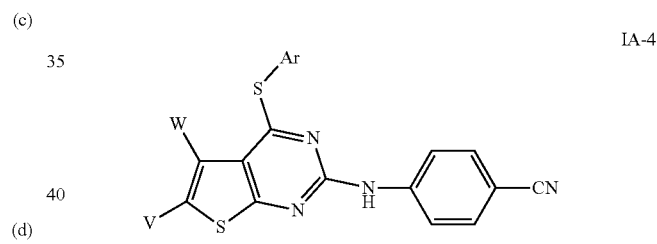

IA-4 or a pharmaceutically acceptable salt thereof.

7. The compound of claim 5 or claim 6, wherein Ar is

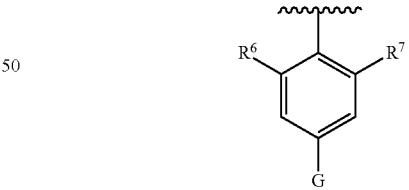

wherein
$R^6$ is selected from H, F, Cl, Br, $CH_3$, $CF_3$, $CH_2F$, $CHF_2$, isopropyl, cyclopropyl, $OCH_3$, OH, $OCF_3$, $NH_2$ and $NHCH_3$;
$R^7$ is Cl, Br, I, $CH_3$, $CF_3$, $OCH_3$, isopropyl, cyclopropyl, t-butyl, or cyclobutyl; and
G is cyclopropyl, acetyl, methyl, bromo, or cyano.

8. The compound of claim 7, wherein V is H; and W is H, methyl, F, Cl, or Br.

9. The compound of claim 3 which is a compound of formula IA-2a:

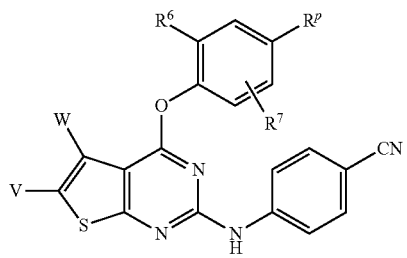

IA-2a or a pharmaceutically acceptable salt thereof.

10. The compound of claim 9, wherein
V is H; and
W is H, F, Cl, Br, methyl, ethyl, or benzyl.

11. The compound of claim 10, wherein W is H, F, Cl, Br, or methyl.

12. The compound of claim 9, wherein
V is H;
$R^6$ is methyl, methoxy or chloro; and
$R^7$ is 6-methyl, or 6-methoxy.

13. The compound of claim 12, wherein $R^P$ is CN, cyclopropyl, methyl, Br, Cl, CH=CHCN, or acetyl.

14. A compound of formula IB:

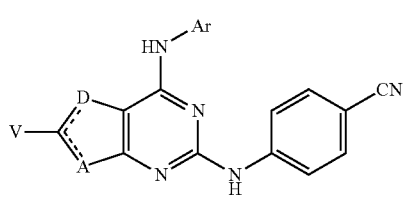

IB wherein:
the dashed line represents a double bond located between C(V) and D;
A is S;
D is C(W);
W is H, F, Cl, Br, C1-C6 alkyl, C2-C6 alkenyl, OC1-C6 alkyl, C3-C6 cycloalkyl, $OC_3$-$C_6$ cycloalkyl, phenyl or benzyl; wherein the alkyl, alkenyl, cycloalkyl, phenyl groups and the phenyl moiety of the benzyl group are optionally substituted with 1-3 groups selected from halogen, $CF_3$, $C_1$-$C_3$ alkyl, and $OC_1$-$C_3$ alkyl;
V is H, halogen or $C_1$-$C_6$ alkyl;
Ar is selected from (a), (b), (c), and (d) below:

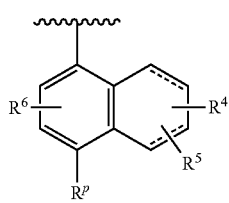

(a)

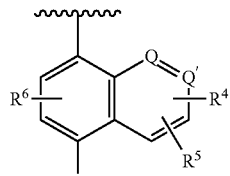

(b)

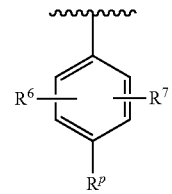

(c)

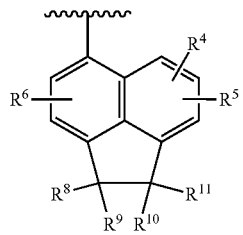

(d)

wherein each $R^P$ is selected from methyl, ethyl, propyl, isopropyl, cyclopropylmethyl, $C_3$-$C_6$ cycloalkyl, cyano, CH=CHCN, Cl, Br, I, acetyl, and $C_1$-$C_6$ alkyl-NH;
$R^4$, $R^5$, and $R^6$ are independently selected from H, F, Cl, Br, $CH_3$, $CF_3$, $CH_2F$, $CHF_2$, isopropyl, cyclopropyl, $OCH_3$, OH, $OCF_3$, $NH_2$, and $NHCH_3$;
or $R^6$ and $R^P$ on adjacent ring atoms, together with the ring atoms to which they are attached, form an additional fused five-membered ring;
Q and Q' are independently selected from N and CH;
$R^7$ is Cl, Br, I, $CH_3$, $CF_3$, $OCH_3$, isopropyl, cyclopropyl, t-butyl, or cyclobutyl; and
$R^8$, $R^9$, $R^{10}$, and $R^{11}$ are each, independently, H or $CH_3$;
or a pharmaceutically acceptable salt thereof.

15. The compound of claim 14 which is a compound of formula IB-1:

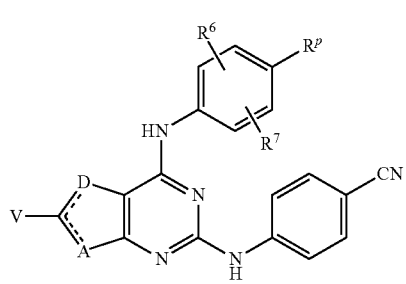

IB-1 or a pharmaceutically acceptable salt thereof.

16. The compound of claim 15, wherein
V is H;
$R^6$ is 2-methyl, 2-methoxy, or 2-chloro; and
$R^7$ is 6-methyl, or 6-methoxy.

17. The compound of claim 16, wherein $R^P$ is CN, cyclopropyl, methyl, Br, Cl, CH=CHCN, or acetyl.

18. A pharmaceutical composition comprising a compound of formula I:

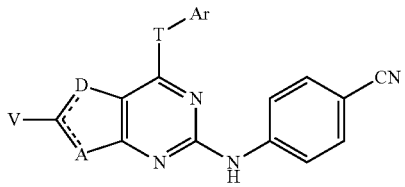

wherein:
the dashed line represents a double bond located between C(V) and D;
A is S;
D is C(W);
T is NH, O, or S;
W is H, F, Cl, Br, C1-C6 alkyl, C2-C6 alkenyl, OC1-C6 alkyl, C3-C6 cycloalkyl, $OC_3$-$C_6$ cycloalkyl, phenyl or benzyl; wherein the alkyl, alkenyl, cycloalkyl, phenyl groups and the phenyl moiety of the benzyl group are optionally substituted with 1-3 groups selected from halogen, $CF_3$, $C_1$-$C_3$ alkyl, and $OC_1$-$C_3$ alkyl;
V is H, halogen, or $C_1$-$C_6$ alkyl;
Ar is selected from (a), (b), (c), and (d) below:

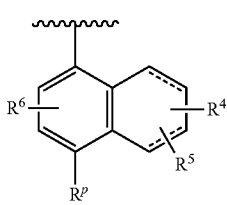
(a)

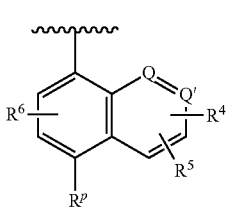
(b)

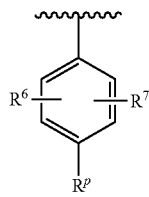
(c)

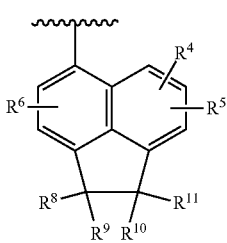
(d)

wherein
each $R^P$ is selected from methyl, ethyl, propyl, isopropyl, cyclopropylmethyl, $C_3$-$C_6$ cycloalkyl, cyano, CH=CHCN, Cl, Br, I, acetyl, and $C_1$-$C_6$ alkyl-NH;

$R^4$, $R^5$, and $R^6$ are independently selected from H, F, Cl, Br, $CH_3$, $CF_3$, $CH_2F$, $CHF_2$, isopropyl, cyclopropyl, $OCH_3$, OH, $OCF_3$, $NH_2$ and $NHCH_3$;
or $R^6$ and $R^P$ on adjacent ring atoms, together with the ring atoms to which they are attached, form an additional fused five-membered ring;
Q and Q' are independently selected from N and CH; and
$R^7$ is Cl, Br, I, $CH_3$, $CF_3$, $OCH_3$, isopropyl, cyclopropyl, t-butyl, or cyclobutyl; and
$R^8$, $R^9$, $R^{10}$, and $R^{11}$ are each, independently, H or $CH_3$;
or a pharmaceutically acceptable salt thereof.

19. A method of inhibiting a human immunodeficiency virus (HIV) comprising contacting said immunodeficiency virus with a compound of formula I, or a pharmaceutically acceptable salt thereof:

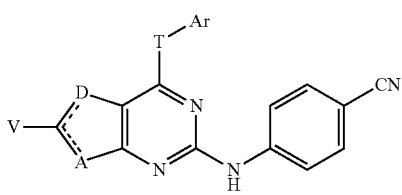

wherein:
the dashed line represents a double bond located between C(V) and D;
A is S;
D is C(W);
T is NH, O, or S;
W is H, F, Cl, Br, $C_1$-$C_6$ alkyl, $C_2$-$C_6$ alkenyl, $OC_1$-$C_6$ alkyl, $C_3$-$C_6$ cycloalkyl, $OC_3$-$C_6$ cycloalkyl, phenyl or benzyl; wherein the alkyl, alkenyl, cycloalkyl, phenyl groups and the phenyl moiety of the benzyl group are optionally substituted with 1-3 groups selected from halogen, $CF_3$, $C_1$-$C_3$ alkyl, and $OC_1$-$C_3$ alkyl;
V is H, halogen, or $C_1$-$C_6$ alkyl;
Ar is selected from (a), (b), (c), and (d) below:

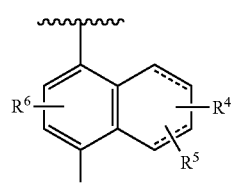
(a)

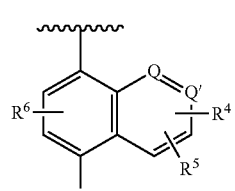
(b)

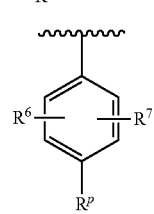
(c)

-continued

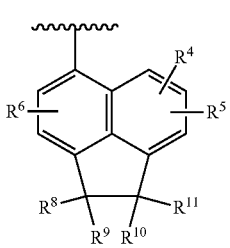
(d)

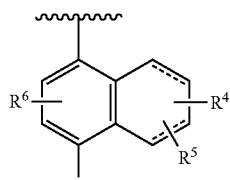
(a)

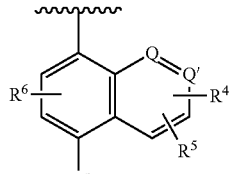
(b)

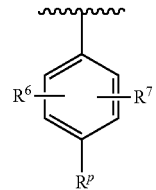
(c)

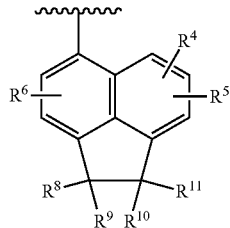
(d)

wherein each $R^P$ is selected from methyl, ethyl, propyl, isopropyl, cyclopropylmethyl, $C_3$-$C_6$ cycloalkyl, cyano, CH=CHCN, Cl, Br, I, acetyl, and $C_1$-$C_6$ alkyl-NH;

$R^4$, $R^5$, and $R^6$ are independently selected from H, F, Cl, Br, $CH_3$, $CF_3$, $CH_2F$, $CHF_2$, isopropyl, cyclopropyl, $OCH_3$, OH, $OCF_3$, $NH_2$ and $NHCH_3$;

or $R^6$ and $R^P$ on adjacent ring atoms, together with the ring atoms to which they are attached, form an additional fused five-membered ring;

Q and Q' are independently selected from N and CH;

$R^7$ is Cl, Br, I, $CH_3$, $CF_3$, $OCH_3$, isopropyl, cyclopropyl, t-butyl, or cyclobutyl; and $R^8$, $R^9$, $R^{10}$, and $R^{11}$ are each, independently, H or $CH_3$.

20. The method of claim 19, wherein said contacting occurs within a cell.

21. A method for treating a human immunodeficiency virus (HIV) infection in a subject, wherein the treating of a human immunodeficiency virus (HIV) infection is alleviating, ameliorating, or inhibiting the human immunodeficiency virus (HIV) infection, the method comprising administering to the subject a pharmaceutically effective amount of a compound of formula I, or a pharmaceutically acceptable salt thereof:

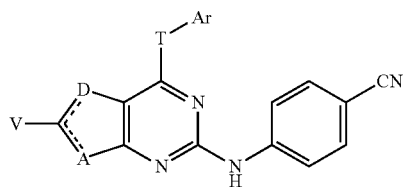
I wherein:

the dashed line represents a double bond located between C(V) and D;

A is S;

D is C(W);

T is NH, O, or S;

W is H, F, Cl, Br, $C_1$-$C_6$ alkyl, $C_2$-$C_6$ alkenyl, $OC_1$-$C_6$ alkyl, $C_3$-$C_6$ cycloalkyl, $OC_3$-$C_6$ cycloalkyl, phenyl or benzyl; wherein the alkyl, alkenyl, cycloalkyl, phenyl groups and the phenyl moiety of the benzyl group are optionally substituted with 1-3 groups selected from halogen, $CF_3$, $C_1$-$C_3$ alkyl, and $OC_1$-$C_3$ alkyl;

V is H, halogen, or $C_1$-$C_6$ alkyl;

Ar is selected from (a), (b), (c), and (d) below:

wherein each $R^P$ is selected from methyl, ethyl, propyl, isopropyl, cyclopropylmethyl, $C_3$-$C_6$ cycloalkyl, cyano, CH=CHCN, Cl, Br, I, acetyl, and $C_1$-$C_6$ alkyl-NH;

$R^4$, $R^5$, and $R^6$ are independently selected from H, F, Cl, Br, $CH_3$, $CF_3$, $CH_2F$, $CHF_2$, isopropyl, cyclopropyl, $OCH_3$, OH, $OCF_3$, $NH_2$ and $NHCH_3$;

or $R^6$ and $R^P$ on adjacent ring atoms, together with the ring atoms to which they are attached, form an additional fused five-membered ring;

Q and Q' are independently selected from N and CH;

$R^7$ is Cl, Br, I, $CH_3$, $CF_3$, $OCH_3$, isopropyl, cyclopropyl, t-butyl, or cyclobutyl; and $R^8$, $R^9$, $R^{10}$, and $R^{11}$ are each, independently, H or $CH_3$.

22. The method of claim 21 wherein said human immunodeficiency virus (HIV) is a drug resistant mutant.

23. The method of claim 21 wherein said human immunodeficiency virus (HIV) is resistant to non-nucleoside reverse transcriptase inhibitors.

24. The method of claim 21 further comprising administering at least one HIV or AIDS drug.

25. The method of claim 21, wherein Ar is (a) or (c).

26. The method of claim 25, wherein $R^6$ is H or a substituent in the 2-position.

27. The method of claim 26, wherein Ar is selected from 4-cyclopropyl phenyl; 4-cyclopropylmethyl phenyl; 4-bromophenyl; 2-chloro-4-bromophenyl; 4-bromo-1-naphthyl; 4-cyclopropyl-1-naphthyl; 2,6-dimethyl-4-cyanophenyl; 2,6-dimethoxy-4-cyanophenyl; 2,6-dimethyl-4-(2-cyanoethenyl) phenyl; 2,6-dimethoxy-4-(2-cyanoethenyl) phenyl; 2-methyl-4-cyclopropyl phenyl; 2,6-dimethyl-4-cyclopropyl phenyl; 2,6-di-trifluoromethyl-4-cyclopropyl phenyl; 2,4,6-trimethyl phenyl; and 2,6-dimethyl-4-acetyl phenyl.

28. The method of claim 21, wherein the compound is a compound of formula IA-2 or formula IA-4:

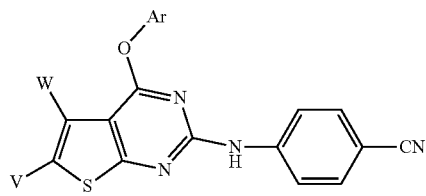

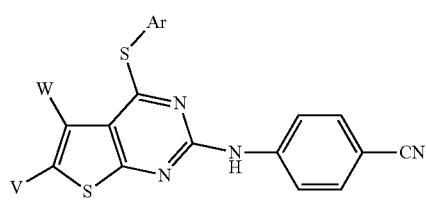

or a pharmaceutically acceptable salt thereof.

29. The method of claim 28, wherein Ar is

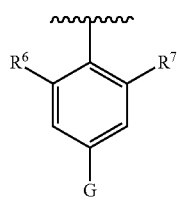

wherein $R^6$ is selected from H, F, Cl, Br, $CH_3$, $CF_3$, $CH_2F$, $CHF_2$, isopropyl, cyclopropyl, $OCH_3$, OH, $OCF_3$, $NH_2$ and $NHCH_3$;

$R^7$ is from Cl, Br, I, $CH_3$, $CF_3$, $OCH_3$, isopropyl, cyclopropyl, t-butyl, or cyclobutyl; and G is cyclopropyl, acetyl, methyl, bromo, or cyano.

30. The method of claim 29, wherein

V is H; and

W is H, methyl, F, Cl, or Br.

31. The method of claim 21, wherein the compound is a compound of formula IA-2a:

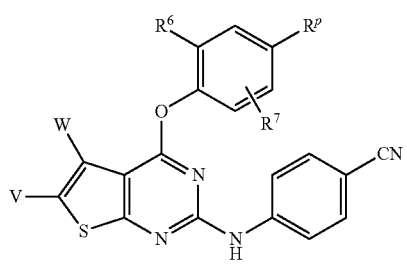

or a pharmaceutically acceptable salt thereof.

32. The method of claim 21, wherein the compound is a compound of formula IB:

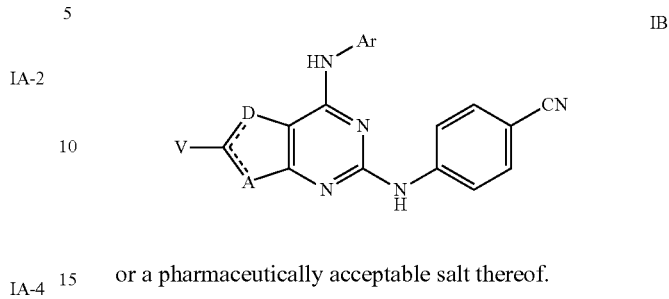

or a pharmaceutically acceptable salt thereof.

33. The method of claim 21, wherein the compound is a compound of formula IB-1:

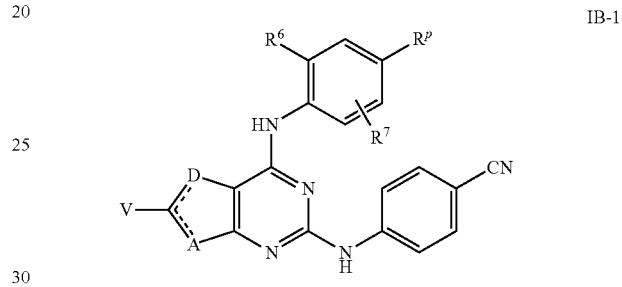

or a pharmaceutically acceptable salt thereof.

34. The method of claim 33, wherein

V is H;

$R^6$ is 2-methyl, 2-methoxy, or 2-chloro; and $R^7$ is 6-methyl, or 6-methoxy.

35. The method of claim 34, wherein $R^P$ is CN, cyclopropyl, methyl, Br, Cl, CH=CHCN, or acetyl.

36. The method of claim 19, wherein Ar is (a) or (c).

37. The method of claim 36, wherein $R^6$ is H or a substituent in the 2-position.

38. The method of claim 37, wherein Ar is selected from 4-cyclopropyl phenyl; 4-cyclopropylmethyl phenyl; 4-bromophenyl; 2-chloro-4-bromophenyl; 4-bromo-1-naphthyl; 4-cyclopropyl-1-naphthyl; 2,6-dimethyl-4-cyanophenyl; 2,6-dimethoxy-4-cyanophenyl; 2,6-dimethyl-4-(2-cyanoethenyl) phenyl; 2,6-dimethoxy-4-(2-cyanoethenyl) phenyl; 2-methyl-4-cyclopropyl phenyl; 2,6-dimethyl-4-cyclopropyl phenyl; 2,6-di-trifluoromethyl-4-cyclopropyl phenyl; 2,4,6-trimethyl phenyl; and 2,6-dimethyl-4-acetyl phenyl.

39. The method of claim 19, wherein the compound is a compound of formula IA-2 or formula IA-4:

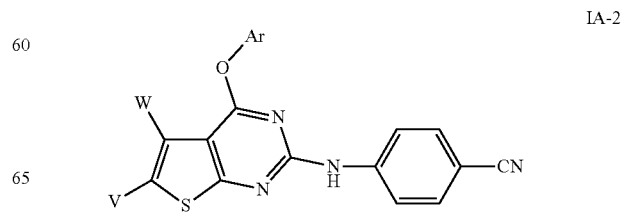

-continued

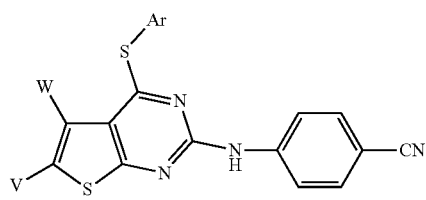

IA-4 or a pharmaceutically acceptable salt thereof.

40. The method of claim 39, wherein Ar is

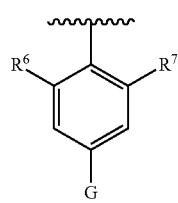

wherein:

$R^6$ is selected from H, F, Cl, Br, $CH_3$, $CF_3$, $CH_2F$, $CHF_2$, isopropyl, cyclopropyl, $OCH_3$, OH, $OCF_3$, $NH_2$ and $NHCH_3$;

$R^7$ is Cl, Br, I, $CH_3$, $CF_3$, $OCH_3$, isopropyl, cyclopropyl, t-butyl, or cyclobutyl; and G is cyclopropyl, acetyl, methyl, bromo, or cyano.

41. The compound of claim 40, wherein

V is H; and

W is H, methyl, F, Cl, or Br.

42. The method of claim 19, wherein the compound is a compound of formula IA-2a:

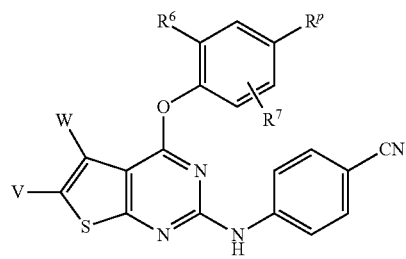

IA-2a or a pharmaceutically acceptable salt thereof.

43. The method of claim 19, wherein the compound is a compound of formula IB:

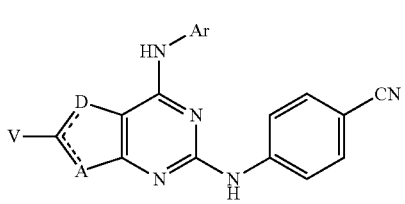

IB or a pharmaceutically acceptable salt thereof.

44. The method of claim 43, wherein the compound is a compound of formula IB-1:

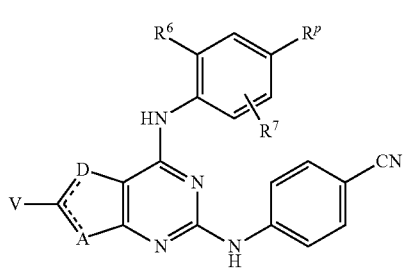

IB-1 or a pharmaceutically acceptable salt thereof.

45. The method of claim 44, wherein

V is H;

$R^6$ is 2-methyl, 2-methoxy, or 2-chloro; and $R^7$ is 6-methyl, or 6-methoxy.

46. The method of claim 45, wherein $R^p$ is CN, cyclopropyl, methyl, Br, Cl, CH=CHCN, or acetyl.

* * * * *